United States Patent
Hsu et al.

(10) Patent No.: US 9,533,046 B2
(45) Date of Patent: *Jan. 3, 2017

(54) CONTROLLED RELEASE FORMULATIONS OF LEVODOPA AND USES THEREOF

(71) Applicant: Impax Laboratories, Inc., Hayward, CA (US)

(72) Inventors: Ann Hsu, Los Altos Hills, CA (US); Jim Kou, San Jose, CA (US); Laman Alani, Fort Worth, TX (US)

(73) Assignee: Impax Laboratories, Inc., Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/958,975

(22) Filed: Dec. 4, 2015

(65) Prior Publication Data

US 2016/0089438 A1   Mar. 31, 2016

Related U.S. Application Data

(63) Continuation of application No. 14/030,813, filed on Sep. 18, 2013, which is a continuation of application (Continued)

(51) Int. Cl.
*A61K 31/185* (2006.01)
*A61K 9/24* (2006.01)
(Continued)

(52) U.S. Cl.
CPC .............. *A61K 47/12* (2013.01); *A61K 9/0002* (2013.01); *A61K 9/1652* (2013.01);
(Continued)

(58) Field of Classification Search
USPC .................................. 424/472, 470
See application file for complete search history.

(56) References Cited

U.S. PATENT DOCUMENTS

| 4,367,217 A | 1/1983 | Gruber et al. |
| 4,427,648 A | 1/1984 | Brickl et al. |

(Continued)

FOREIGN PATENT DOCUMENTS

| AU | 2004270174 | 11/2010 |
| EP | 0253490 | 1/1988 |

(Continued)

OTHER PUBLICATIONS

Nyholm, Dag, "Phamacotherapy for Parkinson's Disease—Observations and Innovations," Comprehensive Summaries of Uppsala Dissertations from the Faculty of Medicine 1236, 2003.

(Continued)

*Primary Examiner* — San-Ming Hui
(74) *Attorney, Agent, or Firm* — Florek & Endres PLLC

(57) ABSTRACT

The current invention provides a controlled release oral solid formulation of levodopa comprising levodopa, a decarboxylase inhibitor, and a carboxylic acid. Also provided by this invention is multiparticulate, controlled release oral solid formulations of levodopa comprising: i) a controlled release component comprising a mixture of levodopa, a decarboxylase inhibitor and a rate controlling excipient; ii) a carboxylic acid component; and iii) an immediate release component comprising a mixture of levodopa and a decarboxylase inhibitor.

31 Claims, 13 Drawing Sheets

Related U.S. Application Data

No. 13/711,248, filed on Dec. 11, 2012, now Pat. No. 8,557,283, which is a continuation of application No. 12/599,668, filed as application No. PCT/US2008/014080 on Dec. 26, 2008, now Pat. No. 8,377,474.

(60) Provisional application No. 61/009,457, filed on Dec. 28, 2007.

(51) Int. Cl.

| | |
|---|---|
| A61K 9/26 | (2006.01) |
| A61K 47/12 | (2006.01) |
| A61K 9/16 | (2006.01) |
| A61K 9/20 | (2006.01) |
| A61K 9/28 | (2006.01) |
| A61K 9/50 | (2006.01) |
| A61K 31/137 | (2006.01) |
| A61K 31/198 | (2006.01) |
| A61K 45/06 | (2006.01) |
| C07C 229/36 | (2006.01) |
| A61K 9/00 | (2006.01) |
| A61K 31/197 | (2006.01) |
| A61K 47/34 | (2006.01) |
| A61K 47/38 | (2006.01) |

(52) U.S. Cl.
CPC .......... *A61K 9/2013* (2013.01); *A61K 9/2054* (2013.01); *A61K 9/2077* (2013.01); *A61K 9/2086* (2013.01); *A61K 9/2846* (2013.01); *A61K 9/5026* (2013.01); *A61K 9/5084* (2013.01); *A61K 31/137* (2013.01); *A61K 31/197* (2013.01); *A61K 31/198* (2013.01); *A61K 45/06* (2013.01); *A61K 47/34* (2013.01); *A61K 47/38* (2013.01); *C07C 229/36* (2013.01)

(56) References Cited

U.S. PATENT DOCUMENTS

| | | | |
|---|---|---|---|
| 4,438,091 | A | 3/1984 | Gruber et al. |
| 4,832,957 | A | 5/1989 | Dempski et al. |
| 4,938,968 | A | 7/1990 | Mehta |
| 5,051,262 | A | 9/1991 | Panoz et al. |
| 5,532,274 | A | 7/1996 | Wenzel et al. |
| 5,576,022 | A | 11/1996 | Yang et al. |
| 5,637,320 | A | 6/1997 | Bourke et al. |
| 5,773,031 | A | 6/1998 | Shah et al. |
| 5,840,756 | A | 11/1998 | Cohen et al. |
| 6,126,969 | A | 10/2000 | Shah et al. |
| 6,194,000 | B1 | 2/2001 | Smith et al. |
| 6,372,252 | B1 | 4/2002 | Blume et al. |
| 6,531,153 | B2 | 3/2003 | Seth |
| 6,627,223 | B2 | 9/2003 | Percel et al. |
| 6,793,936 | B2 | 9/2004 | Devane et al. |
| 6,811,794 | B2 | 11/2004 | Burnside et al. |
| 7,048,945 | B2 | 5/2006 | Percel et al. |
| 7,094,427 | B2 | 8/2006 | Han et al. |
| 2001/0046964 | A1 | 11/2001 | Percel et al. |
| 2002/0192290 | A1 | 12/2002 | Seth |
| 2003/0147957 | A1 | 8/2003 | Licht et al. |
| 2003/0228360 | A1 | 12/2003 | Han et al. |
| 2004/0028613 | A1 | 2/2004 | Quay |
| 2004/0166159 | A1 | 8/2004 | Han et al. |
| 2005/0070608 | A1 | 3/2005 | Remenar et al. |
| 2005/0147670 | A1 | 7/2005 | Hsu et al. |
| 2005/0203185 | A1 | 9/2005 | Remenar et al. |
| 2006/0013875 | A1 | 1/2006 | Han et al. |
| 2006/0045865 | A1* | 3/2006 | Jacob ............... A61K 9/006 424/78.27 |
| 2007/0003621 | A1 | 1/2007 | Nangia et al. |
| 2007/0148238 | A1 | 6/2007 | Nangia et al. |
| 2007/0190145 | A1 | 8/2007 | Venkatesh et al. |
| 2007/0275060 | A1 | 11/2007 | Befumo et al. |
| 2008/0299204 | A1 | 12/2008 | Nangia et al. |

FOREIGN PATENT DOCUMENTS

| | | |
|---|---|---|
| EP | 0313845 | 5/1989 |
| EP | 0393572 | 10/1990 |
| EP | 1262198 | 12/2004 |
| EP | 1670450 | 1/2011 |
| WO | 9904765 | 2/1999 |
| WO | 0015197 | 3/2000 |
| WO | 03000018 | 1/2003 |
| WO | 2005023185 | 3/2005 |
| WO | 2005099678 | 10/2005 |
| WO | 2007002516 | 1/2007 |
| WO | 2007002518 | 1/2007 |
| WO | 2007/022956 | 5/2007 |
| WO | 2007/090091 | 11/2007 |

OTHER PUBLICATIONS

Lewitt, Peter et al., "New Developments in Levodopa Therapy," Neurology, 62(1 suppl. 1):S9-S16, 2004.

Han, Chien-Hsuan, Declaration Under 37 U.S.C. §1.132, Oct. 14, 2004.

Hiroshi, Nagayama, et al., "The Effect of Ascorbic Acid on the Pharmacokinetics of Levodopa in Elderly Patients with Parkinson's Disease," Clinical Neuropharmacology, 2004, 27:270-3.

Fincher, Julian H., "Particle Size of Drugs and its Relationship to Absorption and Activity," Journal of Pharmaceutical Sciences, 1968, 57:1825-35.

Actavis Laboratories FL, Inc., Notification of Certification for U.S. Pat. Nos. 9,089,607 and 9,089,608 Pursuant to § 505(j)(2)(B)(ii) of the Federal Food, Drug, and Cosmetic Act, Aug. 13, 2015.

Actavis Laboratories FL, Inc., Notification of Certification for U.S. Pat. Nos. 8,377,474; 8,557,283; 8,454,998; and 7,094,427 Pursuant to § 505(j)(2)(B)(ii) of the Federal Food, Drug, and Cosmetic Act, Aug. 4, 2015.

Impax Laboratories, Inc., Complaint against Actavis Laboratories FL, Inc. and Actavis Pharma Inc., Action for Patent Infringement under the Food and Drug Laws and Patent Laws of the United States, Sep. 17, 2015.

Akhgari, A., et al., "Statistical Optimization of Indomethacin Pellets Coated with Ph- Dependent Methacrylic Polymers for Possible Colonic Drug Delivery," International Journal of Pharmaceutics, 305:22-30 (2005).

Badawy, Sherif I. and Hussain, Munir A., "Microenvironmental pH Modulation in Solid Dosage Forms," Journal of Pharmaceutical Sciences, vol. 96, No. 5, 948-59 (2007).

Bredenberg, Susanne, et al., et al., "An Automatic Dose Dispenser for Microtablets—A New Concept for Individual Dosage of Drugs in Tablet Form," International Journal Pharmaceutics, 261:137-46 (2003).

Cedarbaum, Jesse M., "Clinical Pharmacokinetics of Anti-Parkinsonian Drugs," Clinical Pharmacokinetics, 13(3):141-78 (1987).

Cedarbaum, Jesse M., "The Promise and Limitations of Controlled-Release Oral Levodopa Administration," Clinical Neuropharmacology, 12(3):147-66 (1989).

Chourasia, M.K. and Jain, S.K., "Pharmaceutical Approaches to Colon Targeted Drug Delivery Systems," Journal of Pharmacy and Pharmaceutical Sciences, 6(1):33-66 (2003), http://www.ualberta.ca/~csps/JPPS6(1)/S.Chourasia/colon.htm:33-66.

Cole, Ewart T., et al., "Enteric Coated HPMC Capsules Designed to Achieve Intestinal Targeting," International Journal Pharmaceutics, 231(1):83-95 (2002).

Contin, Manuela, et al., "Pharmacokinetic Optimisation in the Treatment of Parkinson's Disease," Clinical Pharmacokinetics, 30(6):463-81 (1996).

Crevoisier, C., et al., "Bioavailability of L-Dopa after Madopar HBS Administration in Healthy Volunteers," European Neurology, 27(Suppl. 1):36-46 (1987).

(56) References Cited

OTHER PUBLICATIONS

Crevoisier, C., et al., "Comparative Single- and Multiple-Dose Pharmacokinetics of Levodopa and 3-O-Methyldopa Following a New Dual-Release and a Conventional Slow-Release Formulation of Levodopa and Benserazide in Healthy Volunteers," European Neurology, 49(1):39-44 (2003).

Dave, Mital H., et al., "Expression of Heteromeric Amino Acid Transporters along the Murine Intestine," J Physiol 558.2, 597-610 (2004).

Dingemanse, J., et al., "Pharmacokinetic Studies with a Dual-Release Formulation of Levodopa, a Novel Principle in the Treatment of Parkinson's Disease," European Neurology, 39(2):119-24 (1998).

Espinoza, Rogelio, et al., "Influence of Admixed Citric Acid on the Release Profile of Pelanserin Hydrochloride from HPMC Matrix Tablets," Internatlional Journal Pharmaceutics, 201(2):165-73 (2000).

Gomes, P. and Soares-da-Silva, P., "Na+-Independent Transporters, LAT-2 and B0,+, Exchange L-DOPA with Neutral and Basic Amino Acids in Two Clonal Renal Cell Lines," Journal Membrane Biology, 186(2):63-80 (2002).

Gomes, Pedro and Soares-da-Silva, P., "L-DOPA Transport Properties in an Immortalised Cell Line of Rat Capillary Cerebral Endothelial Cells, RBE 4," Brain Research, 829(1-2):143-50 (1999).

Goole, J., et al., "Development and Evaluation of New Multiple-Unit Levodopa Sustained- Release Floating Dosage Forms," International Journal of Pharmaceutics, 334(1-2):35-41 (2007).

Goole, J. et al., "Evaluation and floating enhancement of levodopa sustained release floating minitablets coated with insoluble acrylic polymer," Drug Development and Industrial Pharmacy, 34(8):827-33 (2008).

Guthmann, C., et al., "Development of a Multiple Unit Pellet Formulation for a Weakly Basic Drug," Drug Development and Industrial Pharmacy, 33(3):341-49 (2007).

Hörter, D. and Dressman, J.B, "Influence of Physicochemical Properties on Dissolution of Drugs in the Gastrointestinal Tract," Advance Drug Delivery Reviews, 46(1-3):75-87 (2001).

Iida, Aiko, et al., "Improvement of Intestinal Absorption of P-glycoprotein Substrate by Dtartaric Acid," Drug Metabolism and Pharmacokinetics, 21(5):424-8 (2006).

Jenner, Peter, "Avoidance of Dyskinesia: Preclinical Evidence for Continuous Dopaminergic Stimulation," Neurology, 62(Suppl. 1):S47-55 (2004).

Kendall, Richard and Basit, Abdul W., "The Role of Polymers in Solid Oral Dosage Forms," Polymers in Drug Delivery, 35-48 (Ijeoma F. Uchebbo and Andreas G. Schätzlein eds., 2006).

Khor, Soo-Pean and Hsu, Ann, "The Pharmacokinetics and Pharmacodynamics of Levodopa in the Treatment of Parkinson's Disease," Current Clinical Pharmacology, 2(3):234-43 (2007).

Knop, Klaus and Kleinebudde, Peter, "Pharmaceutical Pellets," ExAct, No. 15, Nov. 2005.

Kranz, H., et al., "Development of a Single Unit Extended Release Formulation for ZK 811 752, a Weakly Basic Drug," European Journal of Pharmaceutics Sciences, 26(1):47-53 (2005).

Lees, A.J., "The On-Off Phenomenon," Journal of Neurology, Neurosurgery, and Psychiatry. Special Suppl.ement, 29-37 (1989).

LeWitt, Peter A., "Clinical Studies with and Pharmacokinetic Considerations of Sustained-Release Levodopa," Neurology, 42(Suppl. 1):29-32 (1992).

LeWitt, Peter A., "Levodopa Therapeutics: New Treatment Strategies," Neurology, 43(Suppl. 6):S31-7 (1993).

Li,Bingxin et al., "Enteric-Coated Layered Double Hydroxides as a Controlled Release Drug Delivery System," International Journal of Pharmaceutics, 287(1-2):89-95 (2004).

Lorenzo-Lamosa, M.L., et al., "Design of Microencapsulated Chitosan Microspheres for Colonic Drug Delivery," Journal of Control Release, 52(1-2):109-18 (1998).

MacMahon, D.G., et al., "A Comparison of the Effects o Controlled-Release Levodopa (Madopar CR) with Conventional Levodopa in late Parkinson's Disease," Journal of Neurology, Neurosurgery, and Psychiatry, 53(3):220-23 (1990).

Malcolm, S.L., et al., "Single-Dose Pharmacokinetics of Madopar HBS in Patients and Effect of Food and Antacid on the Absorption of Madopar HBS in Volunteers," European Neurology, 27(Suppl. 1):28-35 (1987).

Mylan Bioequivalence ANDA 75-091 (1998).

Nyholm, Dag and Aquilonius, Sten-Magnus, "Levodopa Infusion Therapy in Parkinson Disease: State of the Art in 2004," Clinical Neuropharmacology, 27(5):245-56 (2004).

Nyholm, Dag, "Pharmacokinetic Optimisation in the Treatment of Parkinson's Disease: An Update," Clinical Pharmacokinetics, 45(2):109-36 (2006).

Nyholm, Dag, et al., "Optimizing Levodopa Pharmacokinetics: Intestinal Infusion Versus Oral Sustained-Release Tablets," Clinical Neuropharmacology, 26(3):156-63 (2003).

Nykänen, P., et al., "Citric Acid as Excipient in Multiple-Unit Enteric-Coated Tablets for Targeting Drugs on the Colon," International Journal Pharmaceutics, 229(1-2):155-62 (2001).

Ogawa, Norio, "Factors Affecting Levodopa Effects in Parkinson's Disease," Acta Med Okayama, 54(3):95-101 (2000).

Pinho, Maria João, et al., "Over-Expression of Renal LAT1 and LAT2 and Enhanced LDOPA Uptake in SHR Immortalized Renal Proximal Tubular Cells," Kidney International, 66(1):216-26 (2004).

Poewe, W.H., et al., "Treatment of Motor Fluctuations in Parkinson's Disease with an Oral Sustained-Release Preparation of L-Dopa: Clinical and Pharmacokinetic Observations," Clinical Neuropharmacology, 9(5):430-9 (1986).

Quiñones, Henry, et al., "The Dopamine Precursor L-Dihydroxyphenylalanine is Transported by the Amino Acid Transporters rBAT and LAT2 in Renal Cortex," American Journal Physiology Renal Physiology, 287(1):F74-80 (2004).

Rao, Shobha S., et al., "Parkinson's Disease: Diagnosis and Treatment," American Family Physician, 74(12): 2047-54 (2006).

Scattergood, Laura K., et al., "Comparative Study of Theoretical Versus Actual Weight Gain for a Surelease® Barrier Membrane on Coated Pellets," www.colorcon.com (2004), mr/poster/SureSpheres/stud_comp_wt_gain_REV/rev1.2009.

Siepe, Stefanie, et al., "Strategies for the Design of Hydrophilic Matrix Tablets with Controlled Microenvironmental pH," International Journal of Pharmaceutics, 316(1-2):14-20 (2006).

Simon, Nicolas, et al., "The Effects of a Normal Protein Diet on Levodopa Plasma Kinetics in Advanced Parkinson's Disease," Parkinsonism Related Disorders, 10(3):137-42 (2004).

Sinemet® Label, 2002.

Tang, Elaine S.K., et al., "Coating of Multiparticulates for Sustained Release" American Journal of Drug Delivery, 3(1):17-28 (2005).

"Treatment of Early Parkinson's Disease," American Family Physician, 72(3):497-500 (2005), http://www.aafp.org/afp/2005/0801/p497.html.

Hsu Declaration, dated Aug. 2, 2005.

* cited by examiner

Figure 2: In-Vivo Plasma Concentration Profiles of PK Study IPX066-B05-07

Figure 3: In-Vivo Plasma Concentration Profiles of PK Study IPX066-B06-02 Dissolution

Three 066 Studies Showed Robust Lower Intrasubject Variability Than Sinemet CR

| Study | N | Population | Infusion | IR Q2-3hr | IPX066 | CR |
|---|---|---|---|---|---|---|
| Mouradian | 14 | Patient | 17% | 47% | | |
| IPX066-AH2 | 12 | Healthy* | | | 34% | 47% |
| IPX066-AH4 | 13 | Healthy* | | | 35% | 46% |
| IPX066-AH5 | 15 | Healthy* | | | 31% | 46% |

*Intrasubject variability was obtained by calculating %CV (=Standard deviation/mean) for LD conc determined from Hour 0.5 to Hour 6 (desired dosing interval) after a single dose for each individual subject. The reported value is the mean variability across study population in each study.

Figure 6

CONTROLLED RELEASE FORMULATIONS OF LEVODOPA AND USES THEREOF

This application is a continuation application of U.S. Ser. No. 14/030,813, filed Sep. 13, 2013, which was a continuation application of U.S. Ser. No. 13/711,248, filed Dec. 11, 2012, which was a continuation application of U.S. Ser. No. 12/599,668, filed Nov. 10, 2009, which was an application filed under 35 U.S.C. §371 of PCT application No. PCT/US2008/014080, filed Dec. 26, 2008, which claims the priority of U.S. Ser. No. 61/009,457, filed Dec. 28, 2007, the contents of all of which are hereby incorporated by reference in their entireties into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates to controlled release pharmaceutical compositions of levodopa (LD), formulated with an acid and a decarboxylase inhibitor, to yield enhanced pharmaceutical pharmacokinetic (PK) attributes. These formulations are useful for the treatment of conditions such as neurological diseases associated with reduced or impaired dopamine levels.

BACKGROUND OF THE INVENTION

Combinations of levodopa (LD) and a decarboxylase inhibitor (typically carbidopa (CD)) to treat Parkinson's disease (PD) are known in the pharmaceutical arts and are considered by many to be the 'gold standard' treatment for symptoms of PD. Currently, several formulations containing a combination of LD and CD are commercially available, e.g., Sinemet®, Stalevo®, Parcopa®, and Atamet®. Nonetheless, a need remains for an oral LD formulation that provides steadier plasma concentrations of LD with minimal 'peak-to-trough' fluctuations during daily dosing and that yields a longer duration-of-effect than the currently available oral dosage forms of CD/LD.

Patients suffering from PD frequently have periods in which their mobility becomes difficult, often resulting in an inability to move. Abnormally low levels of dopamine, a neurotransmitter that affects mobility and control of the skeletal-muscular system, is commonly believed to be the cause of these motor symptoms in PD patients. However, administration of dopamine is not effective to treat Parkinson's disease because dopamine does not cross the blood-brain barrier. To resolve this problem, PD patients are administered levodopa, the metabolic precursor of dopamine, but levodopa is not without its issues either.

While levodopa crosses the blood-brain barrier and is rapidly converted to dopamine, LD is problematic because of its rapid decarboxylation by tissues other than the brain. Thus, when LD is administered alone, large doses are required because only a small portion is transported to the brain unchanged. Furthermore, when levodopa is administered orally it is rapidly decarboxylated to dopamine in extracerebral tissues so that only a small portion of a given dose is transported unchanged to the central nervous system. Carbidopa inhibits the decarboxylation of peripheral levodopa and does not cross the blood-brain barrier. Since its decarboxylase inhibiting activity is limited to extracerebral tissues, administration of carbidopa with levodopa has been popular to make levodopa more available for transport to the brain.

In addition to these difficulties associated with absorption of LD, over time patients treated with LD also exhibit symptoms of "wearing off". PD patients treated with LD may develop motor fluctuations characterized by end-of-dose failure, peak dose dyskinesia, and akinesia. The advanced form of motor fluctuations (also commonly referred to as the 'on-off phenomenon) is characterized by unpredictable swings from mobility to immobility. Although the causes of these motor fluctuations are not completely understood, some patients may be attenuated by treatment regimens that produce steady plasma levels of LD. Thus, a void remains in the LD treatment of PD patients, as plasma concentration levels remain difficult to control.

Currently available controlled release formulations of CD/LD are meant to allow for a continuous release of drug over a prolonged period of time in an attempt to maintain tight LD plasma ranges. However, the use of these controlled release dosage forms are problematic in that many PD patients wake up in the morning having little or no mobility due to the wearing off of the dose taken the day/evening before. Once the previous dose has worn off, such patients are usually unwilling, or even unable, to wait for the extended period of time required for a controlled release dosage form to deliver the necessary plasma levels of LD. While the use of an immediate release formulation of LD can reduce this 'wait time', the use of an immediate release formulation of LD require more frequent dosing and are associated with more fluctuating plasma LD concentrations. Duodopa®, an intraduodenal infusion therapy approved outside of the United States, demonstrates significantly reduced motor complications and reduced 'off' time. The cumulative experiences from Duodopa® and experimental infusion studies show that the maintenance of stable plasma LD concentrations and the avoidance of low trough levels appear to be effective in reducing 'off time, increasing 'on' time without disabling dyskinesia, and reduce the severity of dyskinesia in comparison to the standard oral formulations. However, such infusion therapies are extremely inconvenient to the patient.

The results of infusion therapies, such as Duodopa®, strongly suggest a rationale for the development of a LD treatment that provides constant, or relatively steady, LD plasma concentrations to optimize relief of PD symptoms and to minimize 'off' times and dyskinesias. Indeed, a need remains for a more convenient, i.e., oral, dosage form that will improve the administration of LD to PD patients by narrowing blood plasma ranges of LD, which in turn will result in reduced 'off times', prolonged 'on time', and decreased time to 'on'. The present invention fills this void by providing a novel controlled release oral solid dosage form of LD that is formulated with a decarboxylase inhibitor and an acid, to yield the desired pharmacokinetic attributes, i.e., steadier plasma concentrations of LD over a prolonged period of time.

Specifically, the present invention provides an oral pharmaceutical formulation of LD having the following improvements over currently available oral formulations:
a. a faster initial spike of plasma LD, and/or
b. a longer continuous release of LD, over a narrow peak-to-trough ratio (i.e., a flatter plasma profile) to sustain the therapeutic effects and lessen the wearing off effects of LD therapy.

SUMMARY OF THE INVENTION

The current invention provides a controlled release oral solid formulation of levodopa comprising levodopa, a decarboxylase inhibitor, and a carboxylic acid that is not levodopa nor the decarboxylase inhibitor. Also provided by this invention are multiparticulate, controlled release oral solid formulations of levodopa comprising: i) a controlled release component comprising a mixture of levodopa, a decarboxylase inhibitor and a rate controlling excipient; ii) a carboxylic acid component; and iii) an immediate release component comprising a mixture of levodopa and a decarboxylase inhibitor.

The current invention additionally claims a controlled release oral solid formulation of levodopa providing a relative steady levodopa plasma or serum concentration profile over a prolonged period of time; this controlled release oral solid formulation of levodopa having a levodopa plasma or serum concentration profile comprising: a) a time of administration; b) a first concentration; and c) a second concentration, wherein, the first concentration is equal to the maximum concentration of said profile; the second concentration is the minimum concentration occurring at a time later than said first concentration and earlier than or equal to about six hours following the time of administration; and wherein the second concentration is greater than or equal to about fifty percent of the first concentration.

The current invention further relates to an oral dosage form containing CD-LD which would result in a peak-to-trough LD plasma concentration ratio of less than 3, and more preferably less than 2, with a dosing regimen of every six hours (Q6h) or greater. The formulation contains the following constituents: an immediate release dose of CD and LD; one or more modified release doses of CD and LD; and a dose of an organic acid, preferably tartaric acid, that may be coformulated with the modified release component.

Further, the invention provides methods for making and using the pharmaceutical formulations of the invention. Methods for reducing motor fluctuations in a patient suffering from Parkinson's disease, reducing off time in a patient suffering from Parkinson's disease, increasing on time in a patient suffering from Parkinson's disease, reducing time to 'on' in a patient suffering from Parkinson's disease and otherwise enhancing dopamine levels in a subject suffering from a disease associated with reduced or impaired dopamine levels are provided by the presently claimed invention.

BRIEF DESCRIPTION OF DRAWINGS

FIG. 6 is a table showing the robust lower intrasubject variability of the IPX066 formulations compared to Sinemet® CR.

DETAILED DESCRIPTION OF THE INVENTION

Figure 1:
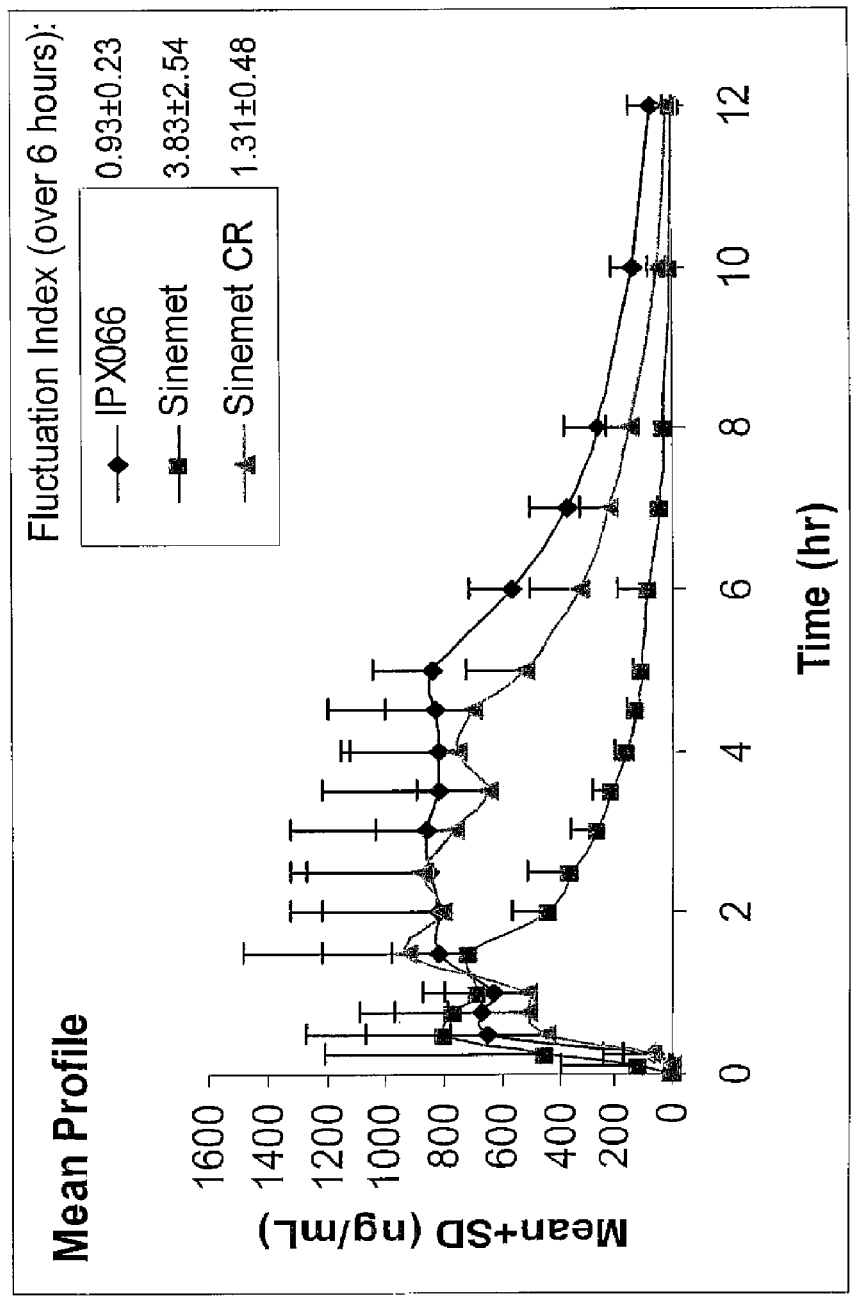
FIG. 1 is a graph showing that IPX066 formulations provide infusion-like plasma profile for longer than about six hours.

The present invention relates to pharmaceutical formulations comprising CD, LD and an acid for treating neurological diseases or conditions associated with reduced or impaired dopamine levels. The pharmaceutical formulations of the invention can be embodied in one or more immediate release (IR) components, one or more modified release components, and an acid component that may or may not be coformulated with a modified release component.

The present invention also relates to controlled release pharmaceutical formulations comprising LD, a decarboxylase inhibitor and a carboxylic acid for treating neurological diseases or conditions associated with reduced or impaired dopamine levels. The pharmaceutical formulations of the invention provide steadier, or more constant, LD plasma concentrations in patients, resulting in decreased motor fluctuations, reduced "off" time and increased "on" time in PD patients.

DEFINITIONS

All scientific and technical terms used in this application have meanings commonly used in the art unless otherwise specified. As used in this application, the following words or phrases have the meanings specified.

The term "acid" refers to a chemical compound that, when dissolved in water, gives a solution with a pH less than 7. The "acid" can be organic. It can have a pKa in the range of e.g., 2-5. Examples of acids suitable for the invention include, but are not limited to, tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic and boric acid or mixtures thereof.

The term "effective amount" means an amount of a compound/composition according to the present invention effective in producing the desired therapeutic effect.

A "tablet" or "pill" comprises a pharmaceutical formulation pressed into a form. The form can be in any shape, for example, round, oblong, triangular or other shapes.

A "capsule" comprises a pharmaceutical formulation in which the pharmaceutical formulation is encased in a hard or soft soluble container. The container can be in the form of gelatin or other material.

The term "modified release" (also known as MR) includes delayed release (also known as DR) and controlled release (also known as CR, sustained release (SR), prolonged release (PR) or extended release (ER)).

The term "delayed release" (also known as DR) relates to a pharmaceutical formulation or component that releases the active ingredients after a period of delay.

The term "controlled release" (also known as CR) refers to a pharmaceutical formulation or component thereof that releases, or delivers, one or more pharmaceutical agents over a prolonged period of time, in this case over a period of more than one hour.

The term "immediate release" (also known as instant release or IR) refers to a pharmaceutical formulation or component thereof which releases, or delivers, one or more pharmaceutical agents substantially immediately upon administration and will result in substantially complete dissolution within about one hour (or less).

The terms "release excipient" or "rate controlling excipient" may be used interchangeably. Release excipients or rate controlling excipients include all excipients and/or polymers that control the release of a pharmaceutical agent(s), e.g., LD, CD and in this case acid, after administration in a subject. Examples of release excipients or rate controlling excipients include, but are not limited to, hypromellose, hydroxypropyl cellulose, ethyl cellulose and prop-2-enoic acid. Delay release polymers, as a subset of release excipients or rate controlling excipients, are used to delay the release of a pharmaceutical agent(s) after administration to a subject. Examples of delay release polymers include, but are not limited to, enteric polymers and/or neutral methacrylic polymers such as Eudragit® L100-55, Eudragit® S100 or Eudragit® FS30D (Rohm).

The "USP paddle method" refers to the Paddle and Basket Method as described in United States Pharmacopoeia, Edition XXII (1990).

The term "peak-to-trough ratio" refers to a comparison of the values for a peak (e.g., a high point in a line graph) plasma level of active agent and a trough (e.g., a low point in a 20 line graph) level over a set amount of time. For example, in a line graph with plasma LD values ranging from 400 ng/ml (peak) compared to 200 ng/ml (trough) over a four hour period, gives a peak-to-trough ratio of 2 for that time. More than one peak-to-trough ratio can be illustrated in a graph.

The term "about" when used in connection with percentages means+/−1%.

The "Mean Plasma Concentration" of a substance (e.g., LD or CD) as used herein, refers to the mean concentration of the substance found in multiple plasma samples. The mean plasma concentration is obtained by adding the concentrations of the substance found in the plasma samples then dividing the sum by the number of plasma samples.

The "upper small intestine" refers to the portion closest to the stomach and includes the duodenum and jejunum.

The term "outer coat" refers to a covering or barrier applied to a pharmaceutical formulation or component thereof and may be an enteric coat.

Diseases associated with reduced or impaired dopamine levels includes neurological or movement disorders such as restless leg syndrome, Alzheimer's disease, dystonia, schizophrenia, Parkinson's disease and secondary parkinsonism, Huntington's disease, Attention-Deficit/Hyperactivity Disorder (ADHD), Shy-Drager syndrome and conditions resulting from brain injury, including carbon monoxide or manganese intoxication.

The term "treating" a disease associated with reduced or impaired dopamine levels, means to manage a disease with the pharmaceutical formulation of the invention. Treatment can decrease the symptoms of a disease, reduce the severity of a disease, alter the course of disease progression, ameliorate and/or cure a disease associated with the neurological or movement disorders associated with reduced or impaired dopamine levels.

COMPOSITIONS OF THE INVENTION

The invention provides pharmaceutical formulations comprising LD, CD, and an acid. A significant aspect of the invention relates to the unexpected discovery of the effect of acids, as defined herein, in enhancing the bioavailability of LD. Examples of suitable acids include, but are not limited to, tartaric acid, adipic acid, succinic acid, citric acid, benzoic acid, acetic acid, alginic acid, ascorbic acid, edetic acid, fumaric acid, lactic acid, malic acid, oleic acid, sorbic acid, stearic acid, and boric acid. The pharmaceutical formulations can include a single acid or a mixture of acids. Preferred acids are tartaric acid and citric acid.

The pharmaceutical formulations of the invention comprise a release rate controlling polymer or a delay release polymer or various combinations and/or mixtures thereof. When orally administered to a subject, the release rate controlling or delay release polymer, or multiple release rate controlling/delay release polymers, liberate the LD, CD and acid over a period of time, e.g., from about 0.01 hours to about 12 hours, including about 0.01 to about 6 hours; or about 0.01 to about 8 hours.

A significant aspect of the invention relates to the unexpected discovery of the effect of carboxylic acid, in controlling the absorption of LD such that the resulting formulations yield 'tighter,' i.e. steadier, LD plasma concentrations.

The invention provides controlled release oral solid formulations of levodopa comprising levodopa, a decarboxylase inhibitor, and a carboxylic acid. In one embodiment of the invention, the carboxylic acid is neither levodopa nor a decarboxylase inhibitor. In accordance with the practice of the invention, the carboxylic acid may be physically separated from the levodopa and the decarboxylase inhibitor. The pharmaceutical formulations can include a single acid or a mixture of acids.

In one embodiment, the carboxylic acid may be a polycarboxylic acid. In another embodiment, the carboxylic acid may be a dicarboxylic acid. Suitable examples of carboxylic acids include, but are not limited to, tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic acid and boric acid or mixtures thereof. In a particular embodiment, the dicarboxylic acid is a tartaric acid.

A suitable example of a decarboxylase inhibitor includes but is not limited to carbidopa.

In accordance with the practice of the invention, the formulation may be a tablet or a caplet. The tablet or caplet may be single-layered or multi-layered. The tablet or caplet may be a matrix tablet or caplet.

Also in accordance with the practice of the invention, the formulation may be a multiparticulate formulation. In an embodiment of the invention, the multiparticulates are encapsulated. In another embodiment, the multiparticulates are not encapsulated. The multiparticulates may be pressed into a tablet. Alternatively, the multiparticulates may be in a sprinkle form that can be sprinkled directly onto food or liquids for easy ingestion.

In an embodiment of the invention, the formulation reduces intrasubject variability in levodopa absorption. The intrasubject variability may be calculated as the standard deviation of the levodopa concentration divided by the mean levodopa concentration determined over the range of about 0.5 hours after administration to about six hours after administration for a single dose of the formulation to an individual subject which when averaged over at least 12 subjects; is less than or equal to about 0.40.

The controlled release oral solid formulation of the invention may comprise carbidopa and levodopa in a ratio of about 1:1 to about 1:10. In one embodiment, the ratio of carbidopa to levodopa is about 1:4.

The controlled release oral solid formulation of the invention may have a ratio of moles of dicarboxylic acid to levodopa of less than 4:1. In one embodiment, the ratio of moles of dicarboxylic acid to levodopa is greater than 1:4 and less than 3:2. In another embodiment, the ratio of moles of dicarboxylic acid to levodopa is greater than 1:2 and less than 4:3. In yet another embodiment, the ratio of moles of dicarboxylic acid to levodopa is greater than 2:3 and less than 5:4. In a further embodiment, the ratio of moles of dicarboxylic acid to levodopa is greater than 1:1 and less than 4:3.

The controlled release oral solid formulation of the invention may comprise from about 25 mg to about 2000 mg levodopa. In one embodiment, the formulation comprises about 50 to 600 mg of levodopa.

The controlled release oral solid formulation of the invention may comprise from about 10 mg to about 300 mg carbidopa. In an embodiment of the invention, the controlled release oral solid formulation comprises about 10 to 80 mg of carbidopa.

The invention also provides multiparticulate, controlled release oral solid formulations of levodopa. A multiparticulate, controlled release oral solid formulation of the invention comprises 1) a controlled release component comprising a mixture of levodopa, a decarboxylase inhibitor and a rate controlling excipient; 2) a carboxylic acid component; and 3) an immediate release component comprising a mixture of levodopa and a decarboxylase inhibitor. In an embodiment of the invention, the decarboxylase inhibitor is carbidopa. The multiparticulate, controlled release oral solid formulation of the invention may reduce intrasubject variability in levodopa absorption.

In accordance with the practice of the invention, the controlled release component may be a distinct component (e.g., separate from the carboxylic acid and immediate release components). In an embodiment of the invention, the carboxylic acid component is a distinct component (e.g., separate from the controlled release and immediate release components). In yet another embodiment, the immediate release component is a distinct component (e.g., separate from the controlled release and carboxylic acid components). In still another embodiment of the invention, the controlled release component, the immediate release component and the carboxylic acid component are each manufactured as distinct, separable beads.

In an embodiment of the invention, all of the components (namely, the controlled release, carboxylic acid, and immediate release components) of the multiparticulate, controlled release oral solid formulation are coformulated into a single component.

The multiparticulate, controlled release oral solid formulation of the invention may further comprise one or more controlled release carboxylic acid components comprising a carboxylic acid and a rate controlling excipient. Suitable examples of carboxylic acids include but are not limited to tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic acid and boric acid or mixtures thereof. In a particular embodiment, the carboxylic acid is tartaric acid. Further, the controlled release carboxylic acid components may comprise a carboxylic acid core coated with one or more enteric polymers. In a particular embodiment, the multiparticulate, controlled release oral solid formulation has at least two controlled release carboxylic acid components that release the carboxylic acid at different rates.

In accordance with the practice of the invention, the rate controlling excipient of the multiparticulate, controlled release oral solid formulation may be an enteric polymer or a mixture of more than one type of enteric polymer. In one embodiment, the rate controlling excipient is a neutral methacrylic polymer.

Embodiments of the pharmaceutical formulations of the invention may contain an immediate release and at least one modified release component. For example, the pharmaceutical formulation may comprise two modified release components, three modified release components, four modified release components or five modified release components. The modified release component(s) may comprise an agent that is formulated with a release controlling or delayed release polymer or the modified release component(s) may comprise an immediate release core that is coated with a release rate controlling or delayed release polymer. The agent may be CD/LD or the acid or CD/LD and the acid. In certain embodiments of the invention, the pharmaceutical formulation comprises an immediate release component of CD and LD and one or more modified release components, at least one of these modified release components containing CD and LD and at least one of which containing the acid. In certain preferred embodiments, the modified release components are each enterically coated and/or further collectively enterically coated, the enteric coating controlling the release of the combination of CD, LD and/or the acid in the small intestine.

In an embodiment of the multiparticulate, controlled release oral solid formulation of the invention, the controlled release component further comprises a carboxylic acid. The carboxylic acid may be a dicarboxylic acid.

In an embodiment of the multiparticulate, controlled release oral solid formulation of the invention, the controlled release component comprises a core of levodopa and decarboxylase inhibitor coated with one or more enteric polymers.

In accordance with the practice of the invention, the immediate release component and modified release component(s) may be in the form of a multilayered tablet, a matrix tablet or in the form of multiple types of beads in a capsule, e.g., immediate release beads of CD/LD mixed with enterically coated CD/LD beads and enterically coated acid beads into a capsule. In other capsule embodiments, the modified release beads may comprise a multilayer bead of CD/LD, acid and coated with a release rate controlling polymer.

The multiparticulate, controlled release oral solid formulation provides an embodiment wherein carbidopa and levodopa is present in a ratio of about 1:1 to about 1:10. In one embodiment, the ratio of carbidopa to levodopa is 1:4.

In a specific embodiment, the modified release component can comprise a ratio of CD to LD of about 1:4 sufficient to provide a plasma concentration of LD with a peak-to-trough ratio of less than 3.5, over a time period spanning from about 1 hour to about 6 hours after administration to the subject.

For example, the peak-to-trough ratio can be about 1.5, about 2, about 2.5, about 3 or about 3.5. Alternatively, the range of the peak-to-trough ratio can be from about 1 to about 1.5, about 1.5 to about 2, about 2 to about 2.5, about 2.5 to about 3 or about 3 to about 3.5.

The ratio of the immediate release and modified release components is carefully chosen to provide a fast peak of LD plasma concentration, followed by a sustained, steady plasma profile which is characterized by a peak-to-trough concentration ratio of, for example, less than 3.5, preferably less than 2, with a dosing frequency not more frequent than 6 hours. For example, the frequency of dosing can be about every 6 hours, 6.5 hours, 7, hours, 7.5 hours, 8 hours, 8.5 hours, 9 hours, 9.5 hours, 10 hours 10.5 hours, 11 hours, 11.5 hours, 12 hours or some mixture thereof.

In one embodiment, the immediate release component comprises a ratio of CD to LD of about 1:4 sufficient to provide an initial peak plasma concentration of about 800 ng/ml to about 1600 ng/ml levodopa, within about the first hour after administration to the subject, and the modified release component comprises a ratio of CD to LD of about 1:4 to about 1:10, sufficient to provide a plasma concentration of LD with a peak-to-trough ratio of less than 3.5, over a time period spanning from about 1 hour to about 6 hours after administration to the subject as discussed above.

In a specific embodiment of the invention, the modified release component comprises a 1:4 ratio of CD to LD sufficient to provide a mean plasma concentration of from about 800 ng/ml to about 1600 ng/ml LD about 1 hour after administration to the subject, about 800 ng/ml to about 1000 ng/ml LD about three hours after administration to the subject, and about 200 ng/ml to about 400 ng/ml LD about six hours after administration to the subject, the release rate being chosen such that the peak plasma level of LD in vivo occurs between about 0.1 to 2 hours after administration of the formulation.

A specific embodiment of the invention is a modified release capsule or tablet having a formulation comprising LD, CD and an acid in one or more layers of the beads of the capsule or tablet, wherein said acid is selected from the group consisting of tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic acid and boric acid or mixtures thereof and is in an amount that facilitates absorption of an effective amount of LD thereby providing a mean plasma concentration of about 300 ng/ml to about 500 ng/ml of LD at about 6 hours after administration to the subject.

The multiparticulate, controlled release oral solid formulation of the invention provides an embodiment wherein the ratio of moles of carboxylic acid to levodopa is less than 4:1. In one embodiment, the multiparticulate, controlled release oral solid formulation, has a ratio of moles of carboxylic acid to levodopa of greater than 1:4 and less than 3:2. In another embodiment, the multiparticulate, controlled release oral solid formulation has a ratio of moles of carboxylic acid to levodopa of greater than 1:2 and less than 4:3. In yet another embodiment, the multiparticulate, controlled release oral solid formulation has a ratio of moles of carboxylic acid to levodopa of greater than 2:3 and less than 4:3. In an additional embodiment, the multiparticulate, controlled release oral solid formulation has a ratio of moles of dicarboxylic acid to levodopa of greater than 1:1 and less than 4:3.

The multiparticulate, controlled release oral solid formulation of the invention provides an embodiment comprising from about 25 mg to about 1200 mg levodopa. In one embodiment, the multiparticulate, controlled release oral solid formulation comprises about 50 to about 600 mg of levodopa.

The multiparticulate, controlled release oral solid formulation of the invention provides an embodiment comprising from about 10 mg to about 300 mg carbidopa. In an embodiment, the multiparticulate, controlled release oral solid formulation comprises 20 mg to about 80 mg of carbidopa. The pharmaceutical formulations of the invention can further comprise excipients including, but not limited to, surfactants (ionic and non-ionic), lipophilic vehicles, and hydrophilic vehicles.

In accordance with the practice of the invention, examples of a rate controlling excipient include, but are not limited to, hydroxypropyl cellulose, hypromellose, ethyl cellulose, and prop-2-enoic acid. One suitable example of a prop-2-enoic acid is Carbopol® (Noveon or Dow Chemical Co.). Examples of delay release polymers include a neutral methacrylic polymer such Eudragit® FS30D, Eudragit® SI00, Eudragit® LI00-55 and/or any mixture or combination thereof (Rohm). Eudragit® LI00-55 is an enteric polymer which can be used in coated dosage forms to target the drug release in the upper small intestine where the pH is above 5.5. Eudragit® SI00 can be used to achieve targeted drug release in the lower small intestine to the colon. The modified release components of the formulations of this invention can be formulated with any, and/or a mixture, of the above polymers, to achieve the desired LD plasma concentration profiles. The choice of the polymers that can be used in the invention includes, but is not limited to, Eudragit®, cellulose acetate phthalate, polyvinyl acetate phthalate, hydroxypropyl methylcellulose phthalate, hydroxypropyl methylcellulose acetate succinate LF, hydroxypropyl methylcellulose acetate succinate HF, and others.

The pharmaceutical formulations of the invention can further comprise other excipients commonly known and used by those of skill in the art, including a plasticizer agent (e.g., triethyl citrate), lubricant (such as talc and magnesium stearate), and disintegrant (such as croscarmellose sodium and crospovidone), or any combination thereof.

The formulations of this invention can comprise CD, LD, tartaric acid, and/or any of hydrophilic carriers, lipophilic carriers, and surfactants. The tartaric acid, hydrophilic carriers, lipophilic carriers, and surfactants can be formulated in a range of concentrations, e.g., 10-90%, to achieve the optimal LD plasma concentration profiles of this invention.

The invention provides a controlled release oral solid formulation of levodopa having or exhibiting a levodopa plasma or serum concentration profile, which profile comprises a time of administration, a first concentration and a second concentration. The controlled release oral solid formulation of levodopa may further comprise at least one carboxylic acid, for example, tartaric acid.

In accordance with the practice of the invention the first concentration may be equal to the maximum levodopa plasma or serum concentration of the profile, the second concentration may be the minimum concentration occurring at a time later than said first concentration and earlier than or equal to about six hours following the time of administration. The second concentration may be greater than or equal to about fifty percent of said first concentration.

In one embodiment of the formulation, the levodopa plasma or serum concentration profile is a median levodopa plasma or serum concentration profile. In another embodiment, the levodopa concentration profile is the mean levodopa plasma or serum concentration profile.

In a further embodiment, the levodopa plasma or serum concentration profile further comprises a third concentration. The levodopa profile in this third concentration may be greater than or equal to fifty percent of the first concentration. Further, the third concentration may occur a time earlier than said first concentration and within about ninety minutes of the time of administration. In a specific embodiment, levodopa in the third concentration may be greater than or equal to sixty percent of the first concentration and the second concentration may be greater than or equal to sixty percent of the first concentration.

In accordance with the practice of the invention, the second concentration may be the minimum concentration occurring between one hour after said time of administration and the second time. In one embodiment, the first concentration is between 825 and 1505 ng/mL for a 380 mg dose of levodopa.

The levodopa plasma or serum concentration profile may have a ratio of mean AUC which is measured in units of ng h/mL, to the mass of levodopa in the formulation, where said mass is measured in mg, is between 11:1 and 25:1. In one embodiment, the ratio is between 14:1 and 19:1. Additionally, the levodopa plasma or serum concentration profile may have a ratio of mean AUC which is measured in units of ng h/mL, to said first concentration, where said concentration is measured in units of ng/mL, of between 9:2 and 6:1.

The levodopa plasma or serum concentration profile may have a mean AUC of between 4330 and 8000 ng h/mL for a 380 mg dose of levodopa. In one embodiment, the mean AUC is between 5000 and 7000 ng h/mL for a 380 mg dose of levodopa.

The levodopa plasma or serum concentration profile may have a ratio of the first concentration which is measured in units of ng/mL, to the mass of levodopa in the formulation, where said mass is measured in mg, of between 3:1 and 5:1. In one embodiment, the ratio is between 5:2 and 7:2. In another embodiment, the ratio is greater than or equal to about 3:1.

In one embodiment, the levodopa plasma or serum concentration profile comprises a time of administration, a first concentration at a first time that occurs within one hour of the time of administration; a second concentration at a second time, that occurs after said first time; and a third concentration at a third time, that occurs at least four hours after said second time. The second concentration may be equal to the maximum concentration of levodopa in the profile; the first concentration may be equal to about fifty percent of the second concentration; said third concentration may be equal to about fifty percent of the second concentration.

In another embodiment, the controlled release oral solid formulation has a levodopa plasma or serum concentration profile substantially the same as levodopa formulation IPX066 in FIG. 1 for a 380 mg dose of levodopa, or having a levodopa plasma or serum concentration profile substantially proportional to said formulation in FIG. 1 for a dose other than 380 mg.

In yet another embodiment, the controlled release oral solid formulation has a levodopa plasma or serum concentration profile such that the ratio of the maximum concentration of the profile to the concentration at any time between one hour and seven hours after administration of the formulation is less than or equal to 4:1.

In a further embodiment, the controlled release oral solid formulation of levodopa has a median levodopa plasma or serum concentration profile comprising: a first concentration at a first time; a second concentration at a second time, that occurs within about one hour after said first time; a third concentration at a third time, that occurs at least four hours after said second time; and a maximum concentration. The second concentration may be equal to the maximum concentration of said profile; the first concentration is equal to fifty percent of said second concentration; the third concentration is equal to fifty percent of the second concentration.

Specific Pharmaceutical Formulations of the Invention

In one embodiment, the pharmaceutical formulation comprises CD, LD, hydroxypropyl cellulose, tartaric acid, microcrystalline cellulose, hypromellose, and magnesium stearate.

In another embodiment, the pharmaceutical formulation comprises CD, LD, microcrystalline cellulose, corn starch, croscarmellose sodium, crospovidone, magnesium stearate, tartaric acid, hypromellose, Eudragit® L100 (Rohm GmbH), Eudragit® S100 (Rohm GmbH), triethyl citrate, and talc.

In yet another embodiment, the pharmaceutical formulation comprises CD, LD, microcrystalline cellulose, corn starch, croscarmellose sodium, crospovidone, magnesium stearate, tartaric acid, hypromellose, Eudragit® L100, triethyl citrate, and talc.

The invention further provides pharmaceutical formulations comprising an inner component and an outer coat.

In one embodiment of pharmaceutical formulations having both an inner component and an outer coat, the inner component comprises CD, LD, hydroxypropyl cellulose, Eudragit® L100, Eudragit® S100, triethyl citrate, and talc; and the outer coating comprises tartaric acid, microcrystalline cellulose, ethylcellulose, hypromellose, Eudragit® L100, Eudragit® S100, triethyl citrate, and talc.

In yet another embodiment of pharmaceutical formulations having both an inner component and an outer coat, the inner component comprises CD, LD, hydroxypropyl cellulose, Eudragit® S100, triethyl citrate, and talc; and the outer coating comprises tartaric acid, microcrystalline cellulose, ethylcellulose, hypromellose, Eudragit® S100, triethyl citrate, and talc.

In still another embodiment of pharmaceutical formulations having both an inner component and an outer coat, the inner component comprises CD, LD, microcrystalline cellulose, hypromellose, Eudragit® L100, Eudragit® S100, triethyl citrate, talc, and a magnesium ammonia solution; and the outer coating comprises tartaric acid, microcrystalline cellulose, ethylcellulose, hypromellose, Eudragit® L100, Eudragit® S100, triethyl citrate, talc, and ammonia solution.

Further still, another embodiment of pharmaceutical formulations having both an inner component and an outer coat provides, the inner component comprising CD, LD, microcrystalline cellulose, hypromellose, Eudragit® S100, triethyl citrate, talc, and ammonia solution; and the outer coating comprising tartaric acid, microcrystalline cellulose, ethylcellulose, hypromellose, Eudragit® S100, triethyl citrate, talc, and ammonia solution.

In a further embodiment still of pharmaceutical formulations having both an inner component and an outer coat, the inner component comprises CD, LD, microcrystalline cellulose, hypromellose, Eudragit® FS 30D, triethyl citrate, talc, and ammonia solution; and the outer coating comprising tartaric acid, microcrystalline cellulose, ethylcellulose, hypromellose, Eudragit® FS 30D, triethyl citrate, talc, and ammonia solution.

In one embodiment of the invention the pharmaceutical formulation comprises CD and LD in a ratio from 1:4 to 1:10. For example, CD to LD ratios can be 1:4, 1:5, 1:6, 1:7, 1:8, 1:9 or 1:10. A preferred ratio of CD to LD is 1:4.

In an embodiment of the invention the pharmaceutical formulation comprises LD, CD and tartaric acid in an amount sufficient to provide a mean plasma concentration of LD from about 200 ng/ml to about 1000 ng/ml at about 6 hours after administration to the subject.

In a preferred embodiment of the invention, the mean plasma concentration of LD is from about 300 ng/ml to about 500 ng/ml, at about 6 hours after administration to the subject.

In a preferred embodiment of the invention, the pharmaceutical formulation comprises a 1:4 ratio of CD to LD (e.g., about 50 mg CD and about 200 mg LD) and about 215 mg acid.

The acid can be present in the formulation in an amount sufficient to facilitate absorption of LD into the upper and/or lower GI tract. In a specific embodiment of the invention, the pharmaceutical formulation containing LD and CD comprises about 50-500 mg of acid. For example, the acid can be present in an amount of about 50 mg, 100 mg, 150 mg, 200 mg, 250 mg, 300 mg, 350 mg, 400 mg, 450 mg or 500 mg. Specifically, the acid can be present in an amount of about 215 mg to about 430 mg.

Coating of the Pharmaceutical Formulation

Another aspect of the invention relates to the method of preparation of the enteric coating of the formulations containing an acid, e.g., tartaric acid. The acid causes a slow and variable drug release rate. The prolonged and slow drug release rate may be due to the interference of the dissolution of the enteric coat, affected by the presence of the acid in the core. The interference can be significantly reduced by partially neutralizing the enteric polymers of the coating, for example, by adding a base (e.g., $NH_3$ or $NH_4OH$) to the coating formulation so as to increase the pH of the coating. The neutralizing technique can be equally effective for different enteric polymers including, but not limited to, Eudragit® L100, S100, and FS100.

METHODS OF THE INVENTION

The invention provides a method of enhancing dopamine levels in a subject suffering from a condition associated with reduced or impaired dopamine levels comprising administering to a subject an effective amount of a pharmaceutical formulation of the invention thereby enhancing dopamine levels in the subject suffering from a condition associated with reduced or impaired dopamine levels.

The invention also provides methods for enhancing or maintaining dopamine levels in a subject suffering from a condition associated with reduced or impaired dopamine levels comprising administering to the subject an effective amount of a pharmaceutical formulation of the invention thereby maintaining dopamine levels in the subject suffering from a condition associated with reduced or impaired dopamine levels.

Enhancing or maintaining dopamine levels in a subject can treat the subject suffering from a condition associated with reduced or impaired dopamine levels. Examples of a condition associated with reduced or impaired dopamine levels include, but is not limited to, Alzheimer's disease, dystonia, schizophrenia, and Parkinson's disease.

The invention further provides methods of reducing motor fluctuations in a patient suffering from Parkinson's disease comprising administering to the patient an effective amount of any of the formulations of the invention thereby providing a plasma concentration of levodopa effective to reduce motor fluctuations in the patient. In one embodiment of the invention, the formulation is administered in six-hour intervals.

Additionally provided are methods of reducing off time in a patient suffering from Parkinson's disease comprising administering to the patient an effective amount of any of the formulations of the invention thereby providing a plasma or serum concentration of levodopa effective to reduce off time in the patient.

Further, the invention provides methods of increasing "on" time in a patient suffering from Parkinson's disease comprising administering to the patient an effective amount of any of the formulations of the invention thereby providing a plasma or serum concentration of levodopa effective to increase on time in the patient.

Also provided are methods of reducing time to 'on' (e.g., accelerating the efficacy of levodopa) in a patient suffering from Parkinson's disease comprising administering to the patient an effective amount of any of the formulations of the invention thereby providing a plasma or serum concentration of levodopa effective to reduce the time to on in the patient.

Determining "on" and "off" time can be based on measuring conventional parameters such as the Unified Parkinson's Disease Rating Scale (UPDRS) motor exam, walking time, and/or tapping number. For each of these parameters, definitions of "on" may be based on change from predose measure, and the results analyzed in the standard manner. For example, for the tapping number measure an about 10% change from the average of the predose measurements, may define the time of "on". For walking time, an about 15% change may be used.

In accordance with the practice of the invention, the plasma or serum concentration of levodopa comprises: a controlled release oral solid formulation of levodopa having a levodopa plasma or serum concentration profile comprising: a time of administration; a first concentration, and a second concentration. In one embodiment of the method, said first concentration is equal to the maximum concentration of said profile; said second concentration is the minimum concentration occurring at a time later than said first concentration and earlier than or equal to about six hours following the time of administration; and wherein the second concentration is greater than or equal to about fifty percent of said first concentration. In another embodiment, the second concentration is the minimum concentration occurring between one hour after said time of administration and said second time.

In the method of the invention, the concentration profile may be the median plasma or serum concentration profile. Further, the concentration profile may be the mean plasma or serum concentration profile.

In one embodiment, the concentration profile further comprises a third concentration, wherein said third concentration is greater than or equal to fifty percent of said first concentration and said third concentration occurs at a time earlier than said first concentration and within about ninety minutes of said time of administration. In another embodiment, the third concentration is greater than or equal to sixty percent of said first concentration and said second concentration is greater than or equal to sixty percent of said first concentration.

In accordance with the practice of the invention, the disease includes but is not limited to Alzheimer's disease, dystonia, schizophrenia and Parkinson's disease.

The invention further provides methods of providing a therapeutically effective and stable blood plasma level of levodopa in a subject comprising administering to the subject a therapeutically effective amount of any of the formulations of the invention. In one embodiment, the blood plasma level does not fluctuate more than 40% between 0.5 hours after administration and six hours after administration.

ADVANTAGES OF THE INVENTION

Optimally, after administration to a patient suffering from a condition associated with reduced or impaired dopamine levels, a pharmaceutical formulation of the invention releases LD into the plasma of the patient at a steady or near constant level, i.e., with a low peak-to-trough ratio of LD plasma concentration, without any significant decrease or fluctuation for an extended amount of time, for example, mimicking infusion administration; thereby reducing motor fluctuations or the "on-off" effect associated with fluctuations in plasma LD levels caused by currently available oral dosage forms of CD/LD.

The pharmaceutical formulations of the invention provide a superior plasma LD profile to a patient than currently available oral pharmaceutical formulations. The formulations of the invention are able to provide a significantly smaller peak-to-trough LD plasma concentration ratio (i.e., narrowing the blood plasma ranges of LD after the initial peak) with e.g., Q6h, dosing. Additionally, some embodiments of the pharmaceutical formulations of the invention provide for improvement by increasing the plasma level of LD. The pharmaceutical formulations of the invention also provide narrow ranges of plasma LD levels thereby minimizing the "on-off" effect in some patients. The sustained, steady LD plasma profile of this invention is expected to provide a superior and consistent disease control.

Surprisingly, incorporation of an acid such as tartaric acid in a controlled release formulation of CD-LD with a 6 hour release duration provides a significantly higher bioavailability of LD compared to the same formulation without tartaric acid.

The following examples are presented to illustrate the present invention and to assist one of ordinary skill in making and using the same. The examples are not intended in any way to otherwise limit the scope of the invention.

Example 1

A Tablet of Carbidopa and Levodopa with Tartaric Acid

The bioavailability/pharmacokinetic results of a tablet formulation of the present invention, using 50-200 mg of CD-LD with 215 mg of tartaric acid, were compared to the controlled release version of Sinemet®.

Preparation of a Tablet of CD-LD with Tartaric Acid (IPX066-B05-07)

CD, LD, and hydroxypropyl were charged into a blender and mixed uniformly. The powder mix was then charged in a high shear granulator and granulated with purified water. Drying of the granules was done overnight in an oven at 60±10° C. Dried granules were passed through a 25 mesh screen, then charged and blended with magnesium stearate in a blender.

To prepare the tartaric acid final blend, granular tartaric acid was passed through a 20 mesh screen. The tartaric acid, microcrystalline cellulose, and hypromellose were charged and blended in a high shear mixer and granulated with ethyl alcohol. The resultant granules were dried in fluid bed processor at 55±10° C. The dry granules were passed through a 25 mesh screen then charged and blended with magnesium stearate in a blender.

The final CD/LD and tartaric acid blends were compressed into a tablet.

Resulting Effect of Tartaric Acid on the Pharmacokinetics of Carbidopa-Levodopa 50-200 mg Formulations in Human Subjects

TABLE 1

| Product | Strength (mg) | Dissolution in SGF |
|---|---|---|
| IPX066 CD/LD Tablets containing tartaric acid | 50-200 | Release over 4 hr |
| IPX066 CD/LD Tablets without tartaric acid | 50-200 | Release over 6 hr |
| EPX066 CD/LD Tablets with tartaric acid | 50-200 | Release over 6 hr |
| Sinemet ® CR Tablets[α] | 50-200 | Release over 3 hr |

[α]Merck & Co., Inc., expiration date August 2007

In vitro dissolution profiles of study drugs are listed below. Formulation tables for IPX066-B05 07 A, B and C are shown at the end of this example.

TABLE 2

| Test | Formulation | Tartaric Acid (mg) |
|---|---|---|
| A | bi-layer | 215 |
| B | ER | 0 |
| C | bi-layer | 215 |

| | | Drug release (%); SGF, 50 rpm, USP Apparatus II w/basket sinker | | | | | |
|---|---|---|---|---|---|---|---|
| Test | Compound | 30 | 60 | 120 | 180 | 240 | 360 |
| A | CDP | 16 ± 1.8 | 30 ± 3.5 | 55 ± 6.2 | 73 ± 7.8 | 86 ± 7.5 | 97 ± 3.0 |
|   | LDP | 16 ± 1.8 | 30 ± 3.6 | 54 ± 6.3 | 72 ± 7.9 | 84 ± 7.5 | 95 ± 3.0 |
| B | CDP | 13 ± 0.6 | 22 ± 1.3 | 38 ± 2.5 | 52 ± 3.5 | 64 ± 4.3 | 84 ± 4.7 |
|   | LDP | 13 ± 0.7 | 22 ± 1.5 | 39 ± 2.9 | 53 ± 4.1 | 66 ± 5.0 | 87 ± 5.2 |
| C | CDP | 12 ± 0.9 | 21 ± 2.1 | 39 ± 4.6 | 55 ± 6.3 | 68 ± 6.7 | 86 ± 5.3 |
|   | LDP | 12 ± 1.1 | 21 ± 2.3 | 39 ± 5.0 | 55 ± 6.7 | 68 ± 7.2 | 87 ± 5.9 |

Figure 2:
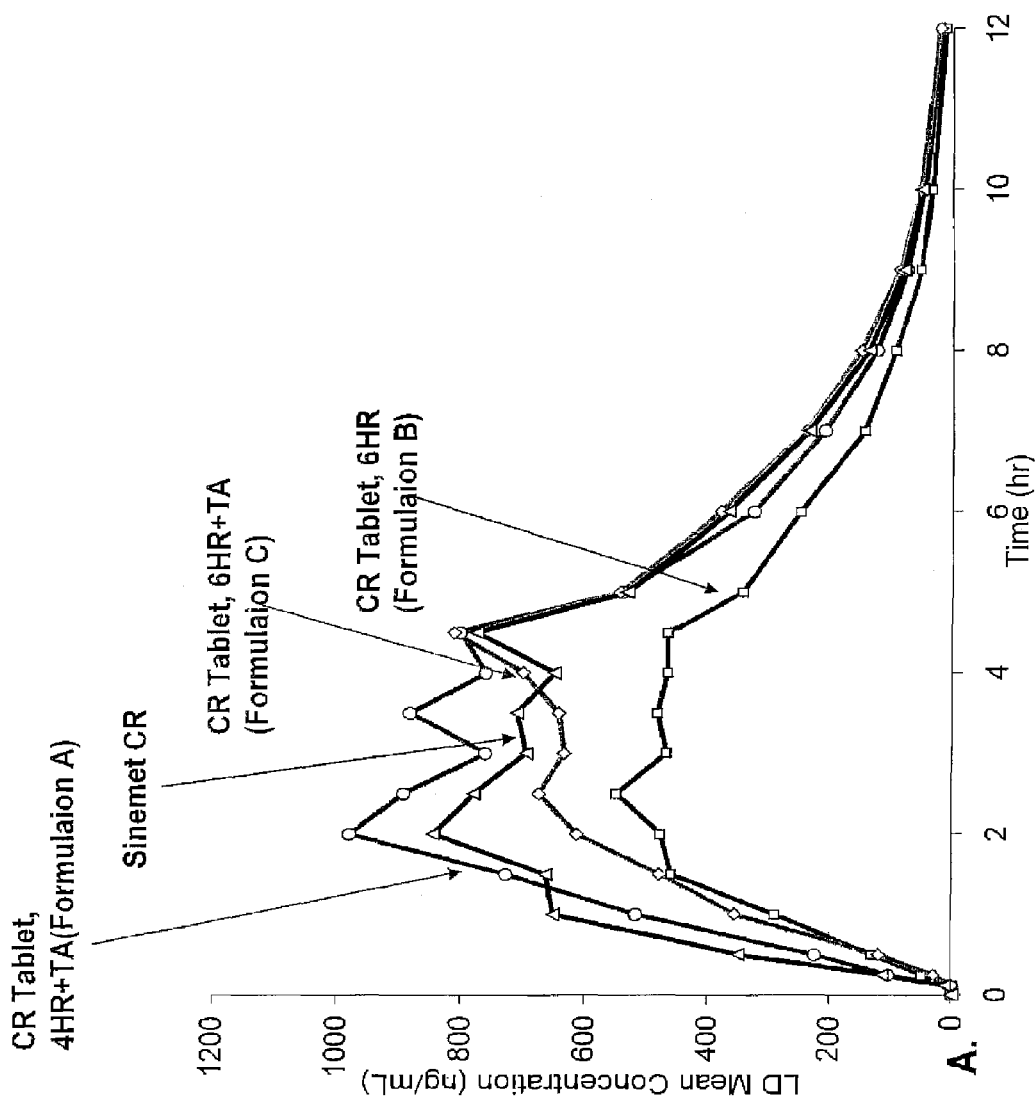
FIG. 2 shows a graph illustrating the in vivo plasma concentration profiles for IPX066-30B-05-07 Formulations A, B and C compared to a reference (Sinemet®), as described in Example 1, infra.

Results and Discussion:

FIG. 2 shows a graph illustrating the in vivo plasma concentration profiles of three formulations of CD, LD with tartaric acid (referred to herein as IPX066-B05-07 formulations A, B and C) compared to Sinemet® after oral administration.

Pharmacokinetics of IPX066 Test B and Sinemet® CR

Following administration of one IPX066 Test B tablet, multiple peaks appeared in the LD plasma profiles, with a maximum plasma concentration ($C_{max}$) occurring at approximately 2.5 hours post dose (FIG. 2). In contrast, CD was slowly absorbed, with median $C_{max}$ occurring at approximately 4 hours post dose. Due to extended dissolution rate, IPX066 Test B with the dissolution rate of 6 hours as opposed to the Reference Sinemet® CR with the dissolution rate of 3 hours decreased by 46% in $C_{max}$ and 44% in AUC of LD, and 38% of $C_{max}$ and 41% in AUC of CD.

Pharmacokinetics of IPX066 Test C and IPX066 Test B

Following administration of one IPX066 Test C tablet, multiple peaks also appeared in the LD plasma profiles, with $C_{max}$ occurring at approximately 3 hours post dose (FIG. 2). In contrast, CD was slowly absorbed, with median $C_{max}$ occurring at approximately 4.5 hours post dose. Even with the extended dissolution rate, IPX066 Test C with the addition of 215 mg of tartaric acid, when compared to IPX066 Test B without the addition of tartaric acid, increased by 50% in $C_{max}$, 41% in AUC, 119% in C6h, and 65% in C8h of LD, and 32% of $C_{max}$ and 35% in AUC of CD Pharmacokinetics of IPX066 Test C and IPX066 Test A Following administration of one IPX066 Test A tablet, multiple peaks also appeared in the LD plasma profiles, with $C_{max}$ occurring at approximately 2 hours post dose (FIG. 2). In contrast, CD was slowly absorbed, with median $C_{max}$ occurring at approximately 4.5 hours post dose. In comparison with IPX066 Test A, IPX066 Test C contained the same amount of tartaric acid and yet a slower dissolution rate by 2 hours. As a result, the LD $C_{max}$, LD AUC, LD C6h, LD C8h, CD $C_{max}$, and CD AUC were reduced by approximately 20%, 14%, 26%, 4%, 22%, and 18%, respectively.

Pharmacokinetics of IPX066 Test A and Sinemet® CR

Following administration of one IPX066 Test A tablet, multiple peaks also appeared in the LD plasma profiles, with $C_{max}$ occurring at approximately 2 hours post dose (FIG. 2). In contrast, CD was slowly absorbed, with median $C_{max}$ occurring at approximately 4.5 hours post dose. BE assessment demonstrated that IPX066 Test A with the dissolution rate of 4 hours and tartaric acid included in formulation is bioequivalent to the Reference Sinemet® CR with the dissolution rate of 3 hours with regard to the $C_{max}$ and AUC values for both LD and CD. In addition, the C6h and C8h of LD of IPX066 Test A were lower than those of Reference Sinemet® CR by approximately 25% and 4%, respectively.

The data herein demonstrated that decreasing dissolution rate decreases the exposure of LD and CD, and addition of tartaric acid increases the $C_{max}$ and AUC of LD and CD.

IPX066-B05-07 Formulation A

| Ingredients | Per Tablet | |
|---|---|---|
| | % (w/w) | Mg |
| Carbidopa | 16.8 | 54.0 |
| Levodopa | 25.47 | 200.0 |
| Hydroxypropyl cellulose (Klucel-LF) | 12.63 | 99.2 |
| Tartaric Acid | 27.38 | 215.0 |
| Microcrystalline cellulose (Avicel PH101) | 21.63 | 169.8 |
| Hypromellose (Methocel K100LV) | 5.48 | 43.0 |
| Magnesium Stearate | 0.53 | 4.2 |
| Total | 100 | 785.2 |

Note:
53.09 mg CD, USP is equivalent to 50.0 mg CD anhydride

IPX066-B05-07 Formulation B

| Ingredients | Per Tablet | |
|---|---|---|
| | % (w/w) | Mg |
| Carbidopa | 16.8 | 54.08 |
| Levodopa | 62.2 | 200.00 |
| Hydroxypropyl cellulose | 20.0 | 64.3 |
| Magnesium Stearate | 1.0 | 3.2 |
| Purified water | — | — |
| Total | 100.0 | 321.5 |

IPX066-B05-07 Formulation C

| Ingredients | Per Tablet | |
|---|---|---|
| | % (w/w) | mg |
| Carbidopa | 6.30 | 54.0 |
| Levodopa | 23.34 | 200.00 |
| Hydroxypropyl cellulose (Klucel-LF) | 19.94 | 170.9 |
| Tartaric Acid | 25.09 | 215.0 |
| Microcrystalline cellulose (Avicel PH101) | 17.82 | 152.7 |
| Hypromellose (Methocel K100LV) | 7.03 | 60.2 |
| Magnesium Stearate | 0.48 | 4.1 |
| Total | 100 | 856.9 |

Note.
53.09 mg CD, USP is equivalent to 50.0 mg CD anhydride

Example 2

Preparation of IPX066-B06-02 Formulations A and B

The following steps were performed to prepare enteric coated pellets containing CD and LD.

CD, LD, and microcrystalline cellulose (Avicel PH-101) were charged and mixed uniformly. The powder mix was charged into a high shear granulator and granulated with purified water. The granulated wet mass was extruded in an extruder with 1.0 mm hole size screen. The extrudate was charged and spheronized in a spheronizer equipped with 3 mm cross-hatch disc. The CD/LD pellets were dried at 60±10° C. in fluid bed processor. The CD/LD pellets were passed through different size screens. The pellets collected were retained on 18 and 25 mesh screens.

The following steps were performed to prepare the enteric coating solution for the CD-LD pellets.

For Formulation IPX066-B06-02 A, Eudragit® S100 and Eudragit® L100 (at the weight ratio of 2:1) and triethyl citrate were dissolved in isopropyl alcohol and acetone solution. The mixture was mixed until dissolved. Talc was dispersed into the polymer solution and mixed continuously throughout the coating process.

For Formulation IPX066-B06-02 B, Eudragit® S100 and triethyl citrate were dissolved in isopropyl alcohol and acetone solution. The mixture was mixed until dissolved. Talc was dispersed into the polymer solution and mixed continuously throughout the coating process.

For both formulations, the CD/LD pellets were spray-coated using the coating dispersion prepared in Glatt GPCG-1 coater. The coated pellets were dried. The dried, coated CD/LD pellets were screened through a 16 mesh screen. The screened CD/LD pellets were charged and blended with talc in a blender.

The following steps were performed to prepare enteric coated pellets containing tartaric acid (TA).

TA was passed through a 20 mesh screen. The screened TA and microcrystalline cellulose (Avicel PH101) were charged in a high shear mixer and granulated with purified water. The granules were extruded in an extruder with 1.0 mm hole size screen. The extrudate was charged and spheronized into a spheronizer equipped with a 3 mm cross hatch disc. The seeds were dried overnight in an oven at 60±10° C. The dried pellets were passed through 16, 18 and 25 mesh screens. The pellets retained were collected on 18 and 25 mesh screens. A seal coat solution was prepared by charging hypromellose (Pharmacoat 606) and ethylcellulose into an alcoholic solution. The mixture was mixed until dissolved. The dried TA pellets were charged in a coater and spray coated with the seal coat solution prepared. The seal coated CD/LD pellets were dried, and passed through a 14 mesh screen.

The following steps were performed to prepare the enteric coating solution for the TA pellets.

For Formulation IPX066-B06-02 A, Eudragit® S100 and Eudragit® L100 (at the weight ratio of 2:1) and triethyl citrate were dissolved in isopropyl alcohol and acetone solution. The mixture was mixed until dissolved. Talc was dispersed into the polymer solution and mixed continuously throughout the coating process.

For Formulation IPX066-B06-02 B, Eudragit® S100 and triethyl citrate were dissolved in isopropyl alcohol and acetone solution. The mixture was mixed until dissolved. Talc was dispersed into the polymer solution and mixed continuously throughout the coating process.

For both formulations, the sealed coated TA pellets were charged in a Glatt GPCG-1 coater and spray coated with the enteric coating solution prepared. The coated TA pellets were dried. The dried, coated TA pellets were passed through a 12 mesh screen. The coated TA pellets were charged and blended with talc in a blender.

The following steps were performed to encapsulate the enteric coated drug pellets and enteric coated TA pellets.

The coated CD/LD pellets prepared as described above and coated TA pellets prepared as described above were encapsulated into hard gelatin capsules. The filled capsules contained 50 mg carbidopa anhydrate, 200 mg LD and 215 mg TA.

Preparation of IPX066-B06-02 Formulations D and E

The following steps were performed to prepare the carbidopa (CD) and levodopa (LD) final blend.

CD, LD, microcrystalline cellulose, and croscarmellose sodium were charged into a blender and mixed uniformly into a powder. Corn starch was dispersed in purified water and stirred for 15 minutes, transferred to boiling water, and stirred continuously until it became starch paste. The spray rate of the peristaltic pump was verified using the starch paste. The powder mix prepared above was charged in a high shear granulator and granulated with starch paste at a flow rate of 50~1000 g/min. The granules were dried in an oven at 60±10° C. until LOD was lower than 3.0%. The dried granules were passed through a 25 mesh screen. The screened CD/LD granules, crospovidone and magnesium stearate were charged and blended in a blender.

To prepare the TA final blend, granular TA was passed through a 20 mesh screen. The TA and microcrystalline cellulose were charged and blended in a high shear mixer and granulated with purified water. The resulting granules were dried in an oven at 60±10° C. until L.O.D. measured by a moisture analyzer was lower than 2.0%. The dry granules were passed through a Fitzmill equipped with a 24 mesh screen. The dried TA granules and magnesium stearate were charged and blended in a blender.

The final blends were compressed into core tablets as follows.

The CD/LD final blend and TA final blend were weighed, mixed and compressed into a tablet. The tablet contained 50 mg carbidopa anhydrate, 200 mg LD and 215 mg TA.

A seal coat was applied to the core tablet by spray coating the core tablet with hypromellose dissolved in the mixture of isopropyl alcohol and purified water solution in Pan Coater. The tablets were dried in the coating pan at 60±10° C. until the L.O.D. was lower than 3.0%.

The enteric coating solution was prepared as follows.

For IPX066-B06-02 Formulation D, Eudragit® S100 and Eudragit® L 100 (at the weight ratio of 0.25:1) and triethyl citrate were dissolved in isopropyl alcohol and acetone solution. The mixture was mixed until dissolved. Talc was dispersed into the polymer solution and mixed continuously throughout the coating process.

For IPX066-B06-02 Formulation E, Eudragit® L100 and triethyl citrate were dissolved in isopropyl alcohol and acetone solution. The mixture was mixed until dissolved. Talc was dispersed into the polymer solution and mixed continuously throughout the coating process.

The sealed coated tablet was charged into a Pan Coater and spray coated with the enteric coating solution prepared. The coated tablet was dried in the coating pan at 40±10° C. for at least 30 minutes.

Resulting Effect of Tartaric Acid and pH of Enteric Coating on the Pharmacokinetics of Carbidopa-Levodopa 50-200 mg Formulations in Human Subjects This study shows the effect of acid addition and of various pH of enteric-coating to carbidopa (CD)/levodopa (LD) 50-200 mg formulation on the PK of CD and LD.

TABLE 3

| Product | Strength (mg') | Enteric Coated pH |
|---|---|---|
| IPX066 CD/LD Capsule with tartaric acid | 50-200 | 6.5 |
| IPX066 CD/LD Capsule with tartaric acid | 50-200 | 7.0 |
| Sinemet ® CR Tablet[a] | 50-200 | N/A |
| IPX066 CD/LD Tablet with tartaric acid | 50-200 | 6.5 |
| IPX066 CD/LD Tablet with tartaric acid | 50-200 | 6.0 |

[a]Merck & Co., Inc., expiration date August 2007

Formulation information of study drugs are listed below. Formulation tables for IPX066-B06-02 A, B, D and E are shown at the end of this example.

Graphs depicting the in vitro dissolution profiles for IPX066-B06-02 A, B, D and E are shown in FIGS. 7, 8, 9 and 10 respectively.

TABLE 4

| Test | Formulation | Particle size (μm) | Tartaric Acid (mg) |
|---|---|---|---|
| A | Capsule | D(v, 0.9) = 36.22<br>D(v, 0.9) = 139.48 | 215 |
| B | Capsule | D(v, 0.9) = 36.22<br>D(v, 0.9) = 139.48 | 215 |
| D | Tablet | D(v, 0.9) = 36.22<br>D(v, 0.9) = 139.48 | 215 |
| E | Tablet | D(v, 0.9) = 36.22<br>D(v, 0.9) = 139.48 | 215 |

Figure 3:
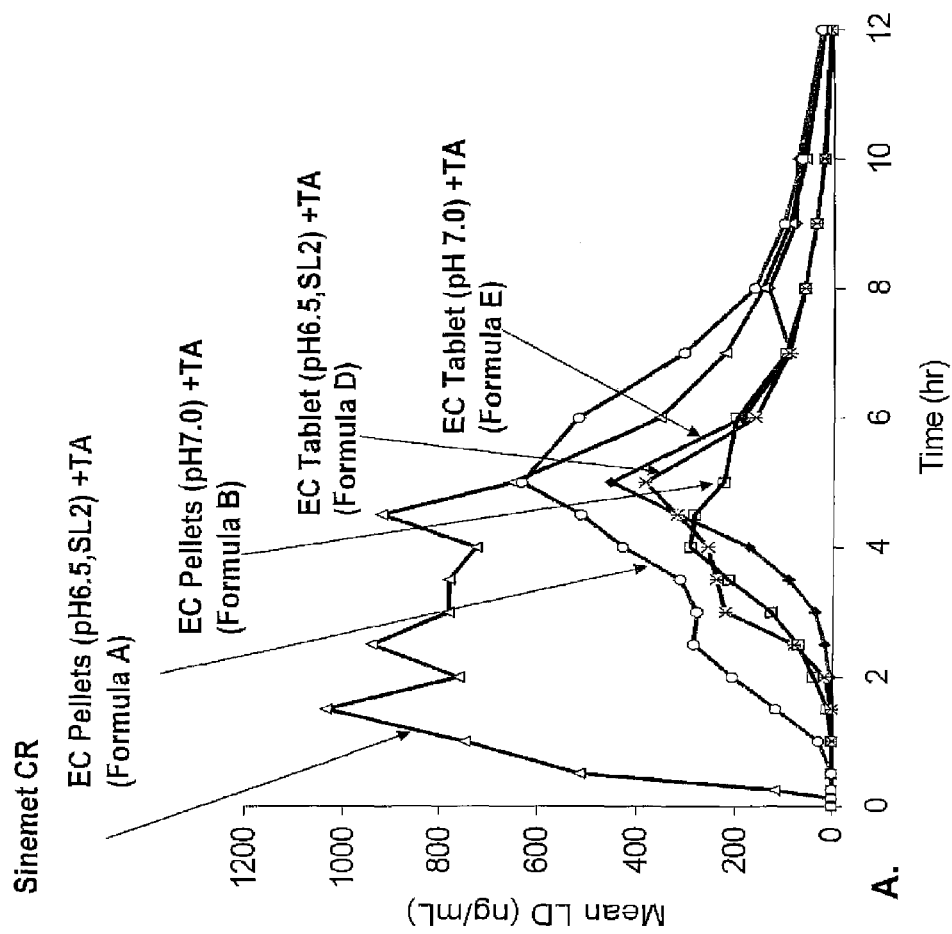
FIG. 3 shows a graph illustrating the in vivo plasma concentration profiles for IPX066-B-06-02 Formulations A, B, D and E compared to a reference (Sinemet®), as described in Example 2, infra.

Results and Discussion:

FIG. 3 show a graph illustrating the in vivo plasma concentration profiles of four formulations of CD, LD and TA (referred to herein as IPX066-B06-02 formulations A, B, D and E) compared to Sinemet® after oral administration.
Pharmacokinetics of IPX066 Test A and Sinemet® CR Following administration of one IPX066 Test A capsule, one peak appeared in the LD median plasma profiles, with a maximum plasma concentration ($C_{max}$) occurring at approximately 5.0 hours post dose (FIG. 3). In contrast, CD was slowly absorbed, with median $C_{max}$ occurring at approximately 6.0 hours post dose. Due to delayed dissolution rate (enteric coated pH=6.5), no LD concentration was observed before 1 hr for IPX066 Test A and the LD concentration of IPX066 Test A between 5 and 8 hr was higher than that of the Reference Sinemet® CR based on the median profile suggesting that addition of TA (215 mg) increase the absorption of LD in the later part of intestine. The AUC of LD for IPX066 Test A was only 58% of that of reference Sinemet® CR.

Pharmacokinetics of IPX066 Test B and Sinemet® CR

Following administration of one IPX066 Test B capsule, one peak also appeared in the LD median plasma profiles, with delayed and lower $C_{max}$ occurring at approximately 4.0 hours post dose (FIG. 3). In contrast, CD was slowly absorbed, with median $C_{max}$ occurring at approximately 4.75 hours post dose. No LD concentration was observed before 2 hr for IPX066 Test B. Even with the addition of TA (215 mg), IPX066 Test B did not have higher LD concentration between 5 and 8 hr when compared to Sinemet® CR. This could be due to the dissolution rate of TA is slower than that of LD. The AUC of LD for IPX066 Test B was only 23% of that of reference Sinemet® CR.

Pharmacokinetics of IPX066 Test D and Sinemet® CR

Following administration of one IPX066 Test D tablet, one peak also appeared in the LD median plasma profiles, with delayed and lower $C_{max}$ occurring at approximately 4.25 hours post dose (FIG. 3). In contrast, CD was slowly absorbed, with median $C_{max}$ occurring at approximately 6.0 hours post dose. No LD concentration was observed before 2 hr for IPX066 Test D. Even with the addition of TA (215 mg), LD AUC of IPX066 Test D was only 24% of that of Reference Sinemet® CR and LD concentration between 5 and 8 hr was lower than that of Sinemet® CR. This is due to the highly variable in vitro dissolution profile and the faster release rate of TA when compared with that of LD.

Pharmacokinetics of IPX066 Test E and Sinemet® CR

Following administration of one IPX066 Test E tablet, one peak also appeared in the LD median plasma profiles, with delayed and lower $C_{max}$ occurring at approximately 4.0 hours post dose (FIG. 3). In contrast, CD was slowly absorbed, with median $C_{max}$ occurring at approximately 5.0 hours post dose. No LD concentration was observed before 2 hr for IPX066 Test E. Even with the addition of tartaric acid (215 mg), LD AUC of IPX066 Test E was only 20% of that of Reference Sinemet® CR and LD concentration between 5 and 8 hr was lower than that of Sinemet® CR. This is also due to the highly variable in vitro dissolution profile and the faster release rate of TA when compared with that of LD.

The data herein demonstrated that delayed dissolution rate decreases the exposure of LD and CD, and addition of TA which has similar dissolution rate to LD and CD has higher LD concentration between 5 and 8 hr when compared to Sinemet® CR.

IPX066-B06-02 Formulation A

| Ingredients | % (w/w) | Amount (mg) |
|---|---|---|
| Carbidopa | 14.06 | 53.98 |
| Levodopa | 52.10 | 200.0 |
| Microcrystalline Cellulose, (Avicel PH-101) | 28.36 | 108.85 |
| Eudragit ® LI00 | 1.14 | 4.39 |
| Eudragit ® SI00 | 2.34 | 8.98 |
| Triethyl Citrate | 1.00 | 3.82 |
| Talc | 1.00 | 3.83 |
| Total | 100.0 | 383.85 |
| Tartaric Acid | 57.6 | 215.0 |
| Microcrystalline Cellulose, NF (Avicel PH-101) | 14.4 | 53.8 |
| Ethylcellulose | 6.6 | 24.8 |
| Hypromellose, Type 2910 | 1.4 | 5.1 |
| Eudragit ® LI00 | 4.6 | 17.2 |
| Eudragit ® SI00 | 9.4 | 35.1 |
| Triethyl Citrate | 4.0 | 14.9 |
| Talc | 2.0 | 7.5 |
| Total | 100.0 | 373.4 |

IPX066-B06-02 Formulation B

| Ingredients | % (w/w) | Amount (mg) |
|---|---|---|
| Carbidopa | 12.92 | 53.98 |
| Levodopa | 47.88 | 200.00 |
| Microcrystalline cellulose (Avicel PHI01) | 26.06 | 108.85 |
| Eudragit ® S100 | 8.85 | 36.95 |
| Triethyl Citrate | 2.53 | 10.55 |
| Talc | 1.76 | 7.37 |
| Total | 100.0 | 417.70 |
| Tartaric Acid | 57.6 | 215.0 |
| Microcrystalline cellulose (Avicel PH101) | 14.4 | 53.8 |
| Ethycellulose | 6.6 | 24.8 |
| Hypromellose, | 1.4 | 5.1 |
| Eudragit ® S100 | 14.0 | 52.3 |
| Triethyl Citrate | 4.0 | 14.9 |
| Talc | 2.0 | 7.5 |
| Total | 100.0 | 373.4 |

IPX066-B06-02 Formulation D

| Ingredients | % (w/w) | mg |
|---|---|---|
| Carbidopa | 8.57 | 53.98 |
| Levodopa | 31.77 | 200.00 |

-continued

| Ingredients | % (w/w) | mg |
|---|---|---|
| Microcrystalline cellulose (Avicel PH101) | 15.17 | 95.5 |
| Corn Starch, | 1.43 | 8.98 |
| Croscarmellose Sodium | 1.43 | 8.98 |
| Crospovidone, | 0.93 | 5.88 |
| Magnesium Stearate | 1.13 | 7.11 |
| Tartaric Acid | 34.15 | 215.0 |
| Hypromellose, type 2910 | 2.93 | 18.42 |
| Eudragit ® Ll00 | 1.40 | 8.82 |
| Eudragit ® S 100 | 0.35 | 2.20 |
| Triethyl Citrate | 0.50 | 3.15 |
| Talc | 0.25 | 1.57 |
| Total | 100.0 | 629.59 |

IPX066-B06-02 Formulation E

| Ingredients | % (w/w) | Amount (mg) |
|---|---|---|
| Carbidopa | 8.57 | 53.98 |
| Levodopa | 31.77 | 200.0 |
| Avicel PH-101 | 15.17 | 95.5 |
| Corn Starch | 1.43 | 8.98 |
| Croscarmellose Sodium | 1.43 | 8.98 |
| Crospovidone | 0.93 | 5.88 |
| Magnesium Stearate | 1.13 | 7.11 |
| Tartaric Acid | 34.15 | 215.00 |
| Hypromellose, Type 2910 | 2.93 | 18.42 |
| Eudragit ® L100 | 1.75 | 11.02 |
| Triethyl Citrate | 0.5 | 3.15 |
| Talc | 0.25 | 1.57 |
| Total | 100.0 | 629.59 |

Example 3

Preparation of IPX066-B07-01 Formulations A, B and C

The following steps were performed to prepare enteric coated pellets containing Carbidopa-Levodopa (CD-LD).

CD, LD, and microcrystalline cellulose (Avicel PH-101) were blended together. The mixture was charged into a high shear granulator and granulated with purified water. The granulated wet mass was extruded in an extruder with 1.0 mm hole size screen. The extrudate was charged and spheronized in a spheronizer equipped with 3 mm crosshatch disc. The spheres obtained from the spheronizer were dried at 60±10° C. in a Glatt GCPG-1 coater. Drying the pellets in the Glatt GPCG-1 eliminated discoloration of the pellets and also reduced the amount of degradation product DHP. The drug-loaded pellets were screened with 16, 18 and 25 mesh screens and the collected pellets retained on 18 and 25 mesh screens. The core pellets were then coated with hypromellose (Pharmacoat 606) aqueous solution in a Glatt GCPG-1 coater. The coated pellets were screened with an 18 mesh screen after they were dried in GPCG-1.

The enteric coating solution was prepared as follows. For formulation IPX066-B07-01 A, Eudragit® S100 and Eudragit® L100 were dispersed separately at the weight ratio of 5:1 into purified water and mixed until a uniform dispersion. 1N NH$_4$OH solution was then added drop-wise to both solutions until the pH reached 5.5. The two solutions were combined together and mixed thoroughly. A talc suspension was prepared by dispersing Talc into triethyl citrate solution in purified water and then stirred for 1 hour. The above mixture of L100 and S100 was then combined with the Talc dispersion and mixed thoroughly. The dispersion was screened through a 140 mesh screen before starting the coating process. For IPX066-B07-01 formulation B, the same procedure was followed for formulation A except using only Eudragit® S100 polymer. For IPX066-B07-01 formulation C, the same procedure was followed for formulation A, except using only Eudragit® FS30D polymer.

The hypromellose coated seeds were spray coated with the enteric coating dispersion preparation. The coated CD/LD pellets were dried in an oven. The dried CD/LD pellets were passed through a 14 mesh screen. The final blend was prepared by blending the screened CD/LD pellets with talc.

The following steps were performed to prepare enteric coated pellets containing TA.

TA was passed through a 20 mesh screen. The screened TA and microcrystalline cellulose (Avicel PH 101) was charged in a high shear mixer and granulated with purified water. The wet mass was extruded in an extruder with 1.0 mm hole size screen. The extrudate was charged and spheronized in a spheronizer equipped with a 3 mm cross hatch disc. The pellets obtained were dried overnight in an oven at 60±10° C. The dried pellets were passed through 16, 18 and 25 mesh screens and the collected pellets retained on 18 and 25 mesh screens. The seal coat solution was prepared by dissolving hypromellose (Pharmacoat 606) and ethylcellulose in alcoholic solution. The seal coat solution was applied to the TA pellets in a Glatt GPCG-1 coater. The pellets were dried in a GPCG-1 and passed through a 14 mesh screen.

The enteric coating solution was prepared as follows. For IPX066-B07-01 formulation A, Eudragit® S100 and Eudragit® L100 were dispersed separately at the weight ratio of 5:1 into purified water and mixed until a uniform dispersion. 1N NH$_4$OH solution was then added drop-wise to both solutions until pH reached 5.5. The two solutions were combined together and mixed thoroughly. A talc suspension was prepared by dispersing Talc into triethyl citrate solution in purified water and then stirred for 1 hour. The above mixture of L100 and S100 was then combined with the Talc dispersion and mixed thoroughly. The dispersion was screened through a 140 mesh screen before starting the coating process. For IPX066-B07-01 formulation B, the same procedure was followed for formulation A, except using only Eudragit® S100 polymer. For IPX066-B07-01 formulation C, the same procedure was followed for formulation A except using only Eudragit® FS30D polymer. The screened tartaric acid pellets were charged in a Glatt GPCG-1 coater and spray coated with the enteric coating dispersion. The coated seeds were dried in oven. The dried, coated pellets were screened through a 14 mesh screen. The final blend was prepared by blending the screened pellets and talc.

The coated CD/LD pellets and coated TA pellets were encapsulated into hard gelatin capsules. The filled capsules contained 50 mg carbidopa anhydride, 200 mg LD and 215 mg TA.

Resulting Effect of Tartaric Acid and pH of Enteric Coating on the Pharmacokinetics of Carbidopa-Levodopa 50-200 mg Formulations in Human Subjects Objectives:

This study tested the effect of acid addition and of various pH of enteric-coating (Eudragit® S100/L100=5, Eudragit® S100 and Eudragit® FS 30D) to carbidopa (CD)/levodopa (LD) 50-200 mg formulation on the PK of CD and LD.

TABLE 5

| Product | Strength (mg) | Enteric Coated Polymer |
|---|---|---|
| LPX066 CD/LD Capsule with tartaric acid | 50-200 | Eudragit ® S100/L100 = 5 |
| IPX066 CD/LD Capsule with tartaric acid | 50-200 | Eudragit ® S100 |
| EPX066 CD/LD Capsule with tartaric acid | 50-200 | Eudragit ® FS 30D |
| Sinemet ® CR Tablet[a] | 50-200 | N/A |

[a]Merck & Co., Inc., expiration date February 2009

Formulation information and in vitro dissolution profiles of study drugs are listed below. Formulation tables for IPX066-B07-01 A, B and C are shown in the end of this example.

Figure 11:
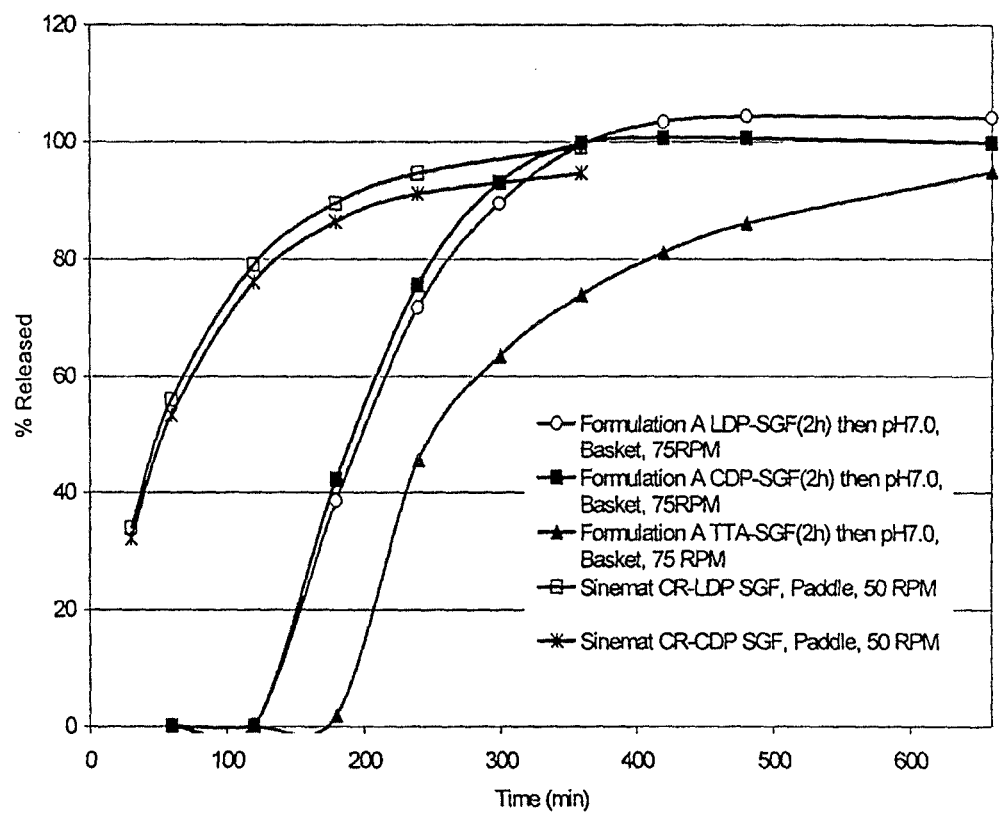
FIG. 11 shows a graph showing the in vitro dissolution profiles of IPX066-B07-01 Formulation A and a reference product (Sinemet®), as described in Example 3, infra.
Figure 12:
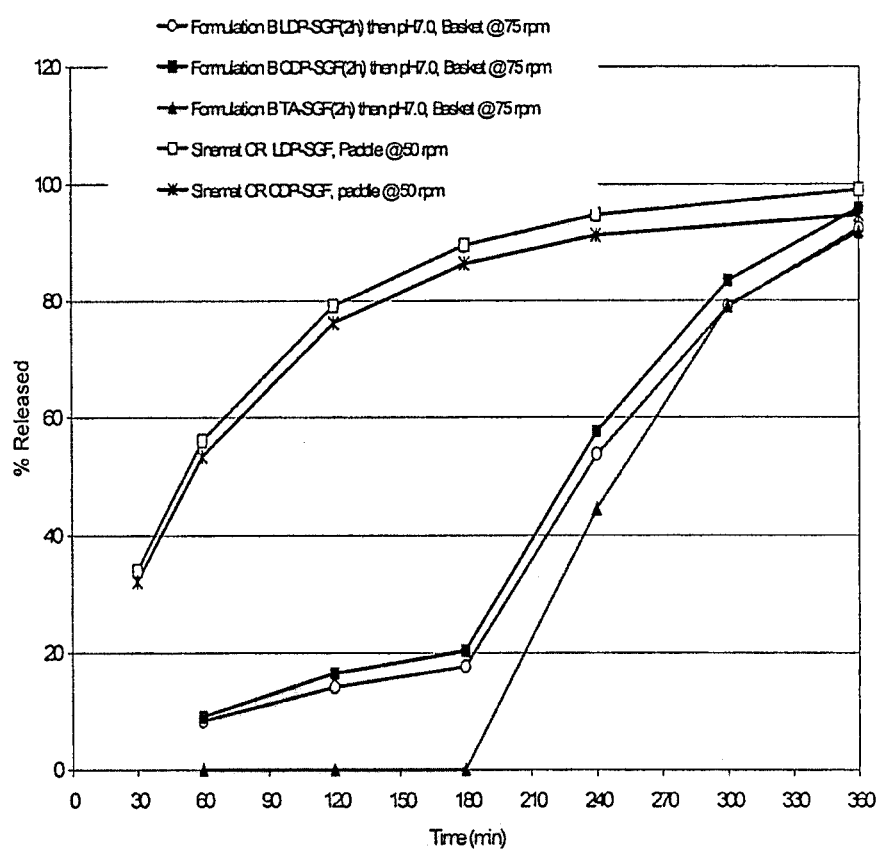
FIG. 12 shows a graph showing the in vitro dissolution profiles of IPX066-B07-01 Formulation B and a reference product (Sinemet®), as described in Example 3, infra.
Figure 13:
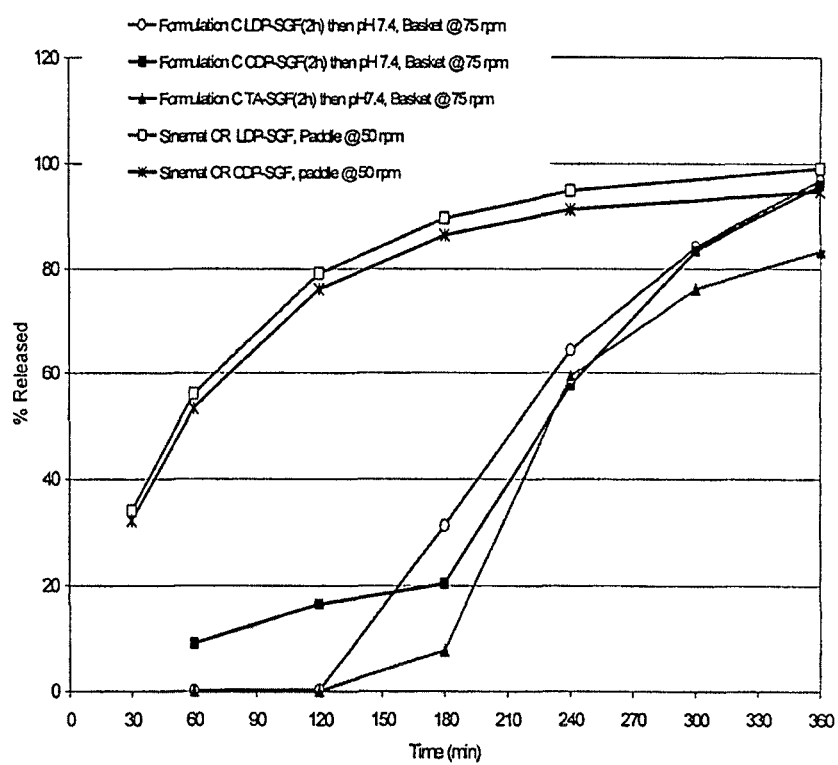
FIG. 13 shows a graph showing the in vitro dissolution profiles of IPX066-B07-01 Formulation C and a reference product (Sinemet®), as described in Example 3, infra.

Graphs depicting the in vitro dissolution profiles for IPX066-B07-01 A, B and C are shown in FIGS. 11, 12 and 13 respectively.

TABLE 6

| Test | Formulation | Particle size (μm) | Tartaric Acid (mg) |
|---|---|---|---|
| A | Capsule | D(v, 0.9) = 36.22<br>D(v, 0.9) = 139.48 | 215 |
| B | Capsule | D(v, 0.9) = 36.22<br>D(v, 0.9) = 139.48 | 215 |
| C | Capsule | D(v, 0.9) = 36.22<br>D(v, 0.9) = 139.48 | 215 |

Figure 4:
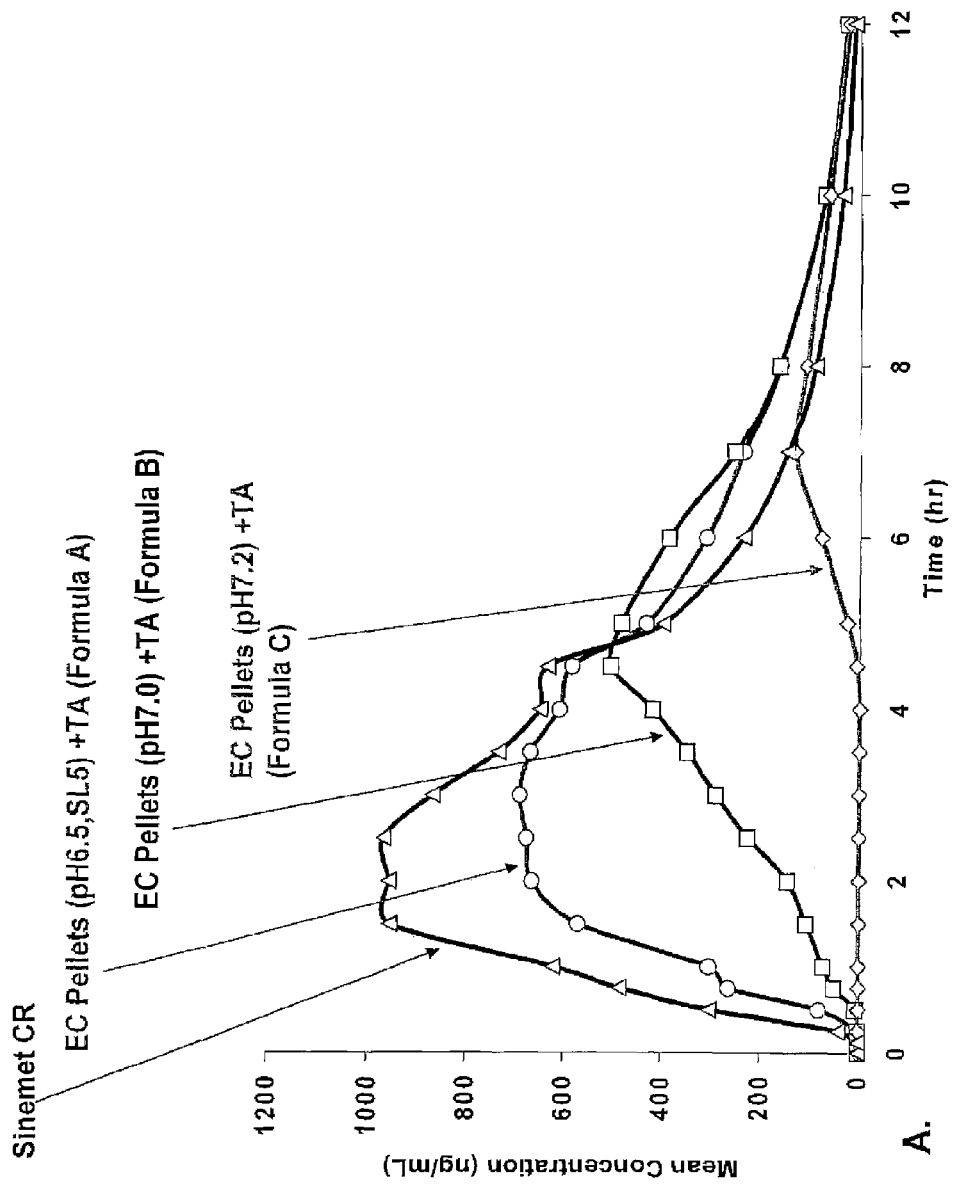
FIG. 4 shows a graph illustrating the in vivo plasma concentration profiles for IPX066-B-07-01 Formulations A, B and C compared to a reference (Sinemet®), as described in Example 3, infra.
Figure 5:
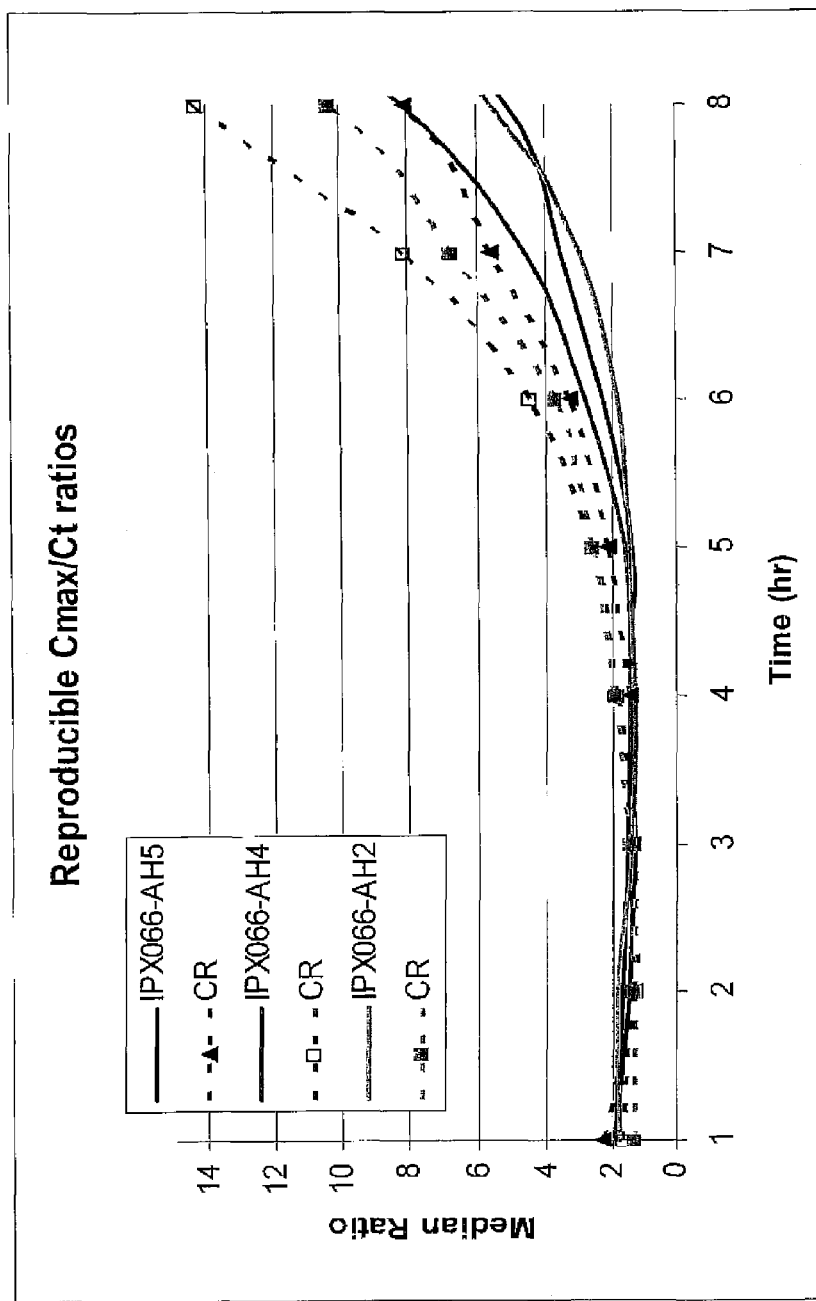
FIG. 5 shows a graph illustrating the in vivo plasma concentration profiles for IPX066 formulations.
Figure 7:
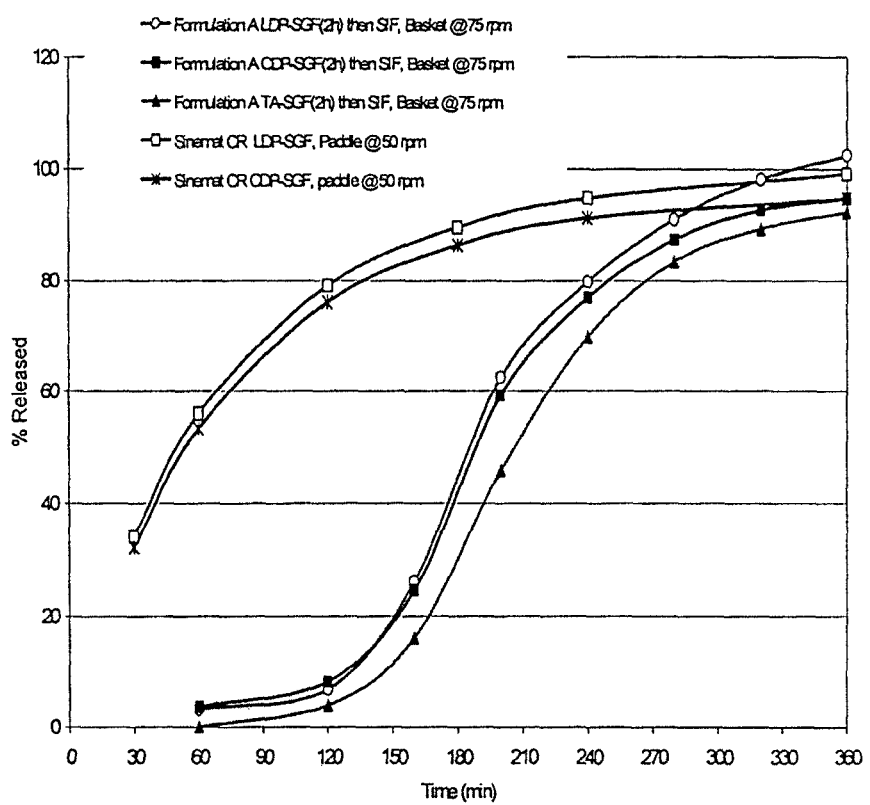
FIG. 7 shows a graph showing the in vitro dissolution profiles of IPX066-B06-02 Formulation A and a reference product (Sinemet®), as described in Example 2, infra
Figure 8:
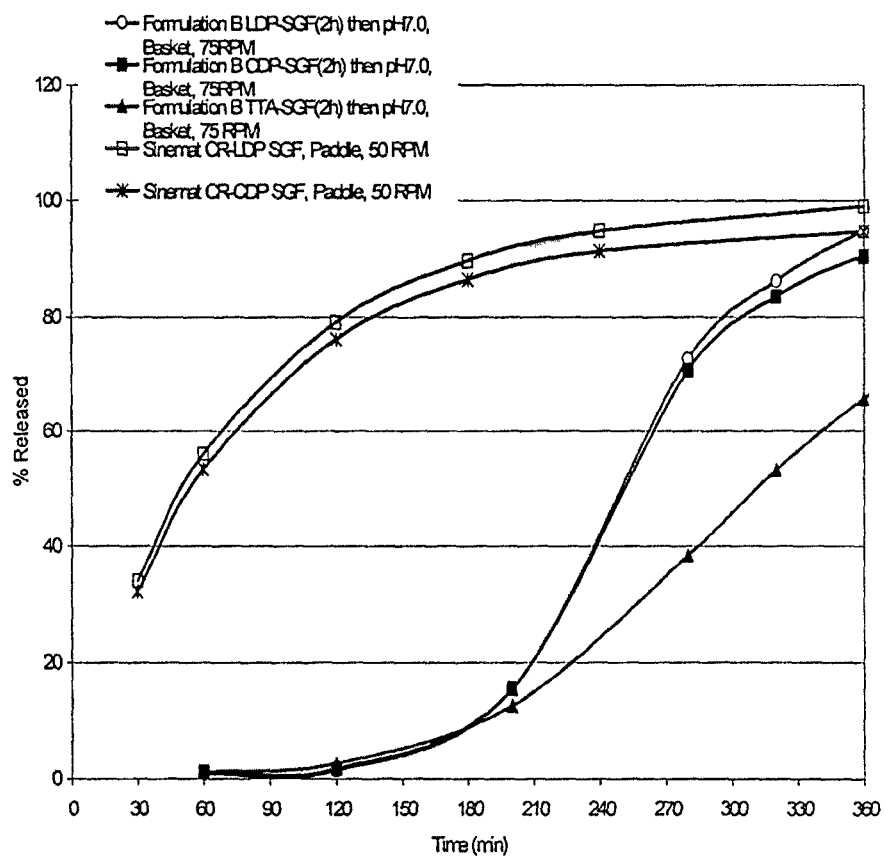
FIG. 8 shows a graph showing the in vitro dissolution profiles of IPX066-B06-02 Formulation B and a reference product (Sinemet®), as described in Example 2, infra
Figure 9:
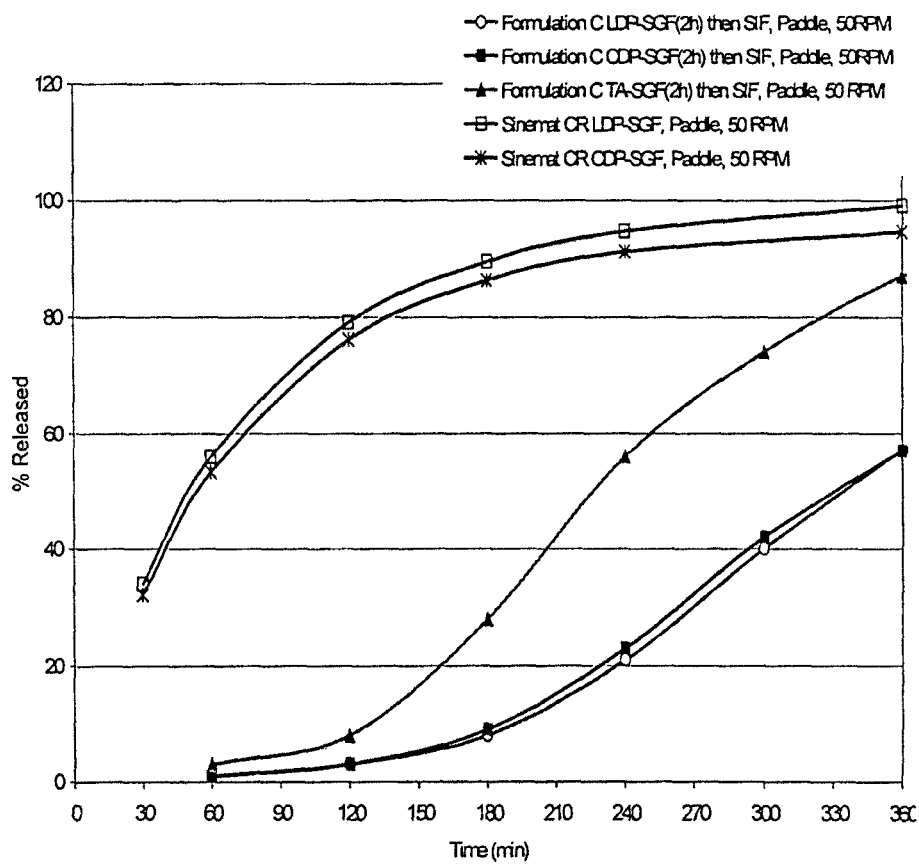
FIG. 9 shows a graph showing the in vitro dissolution profiles of IPX066-B06-02 Formulation C and a reference product (Sinemet®), as described in Example 2, infra
Figure 10:
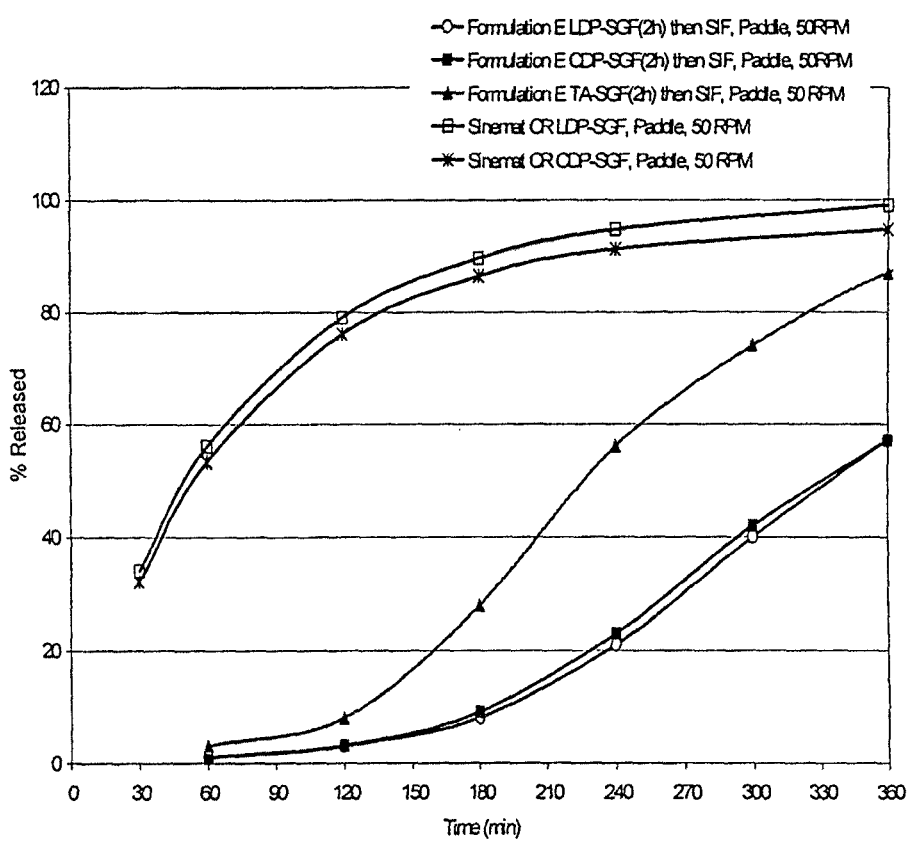
FIG. 10 shows a graph showing the in vitro dissolution profiles of IPX066-B06-02 Formulation D and a reference product (Sinemet®), as described in Example 2, infra.

Results and Discussion:

FIG. 4 shows a graph illustrating the in vivo plasma concentration profiles of three formulations of CD, LD and TA (referred to as IPX066-B07-01 formulations A, B and C) compared to Sinemet® after oral administration.

Pharmacokinetics of IPX066 Test A and Sinemet® CR

Following administration of one IPX066 Test A capsule, one peak appeared in the LD median plasma profiles, with a maximum plasma concentration ($C_{max}$) occurring at approximately 2.75 hours post dose (FIG. 4), and the LD concentration remains at the same level from 2.0 to 3.5 hrs.

In contrast, CD was slowly absorbed, with median $C_{max}$ occurring at approximately 4.0 hours post dose. Due to delayed dissolution rate (enteric coated with Eudragit® S100/L100=5), the absorption of LD (the ascending phase of plasma profile) from IPX066 Test A was slow compared with Sinemet® CR and the LD concentration of IPX066 Test A between 5 and 10 hr was higher than that of the Reference Sinemet® CR based on the median profile suggesting that addition of TA (215 mg) increase the absorption of LD in the lower part of intestine. The AUC of LD for IPX066 Test A was only 87.72% of that of reference Sinemet® CR.

Pharmacokinetics of IPX066 Test B and Sinemet® CR

Following administration of one IPX066 Test B capsule, one peak also appeared in the LD median plasma profiles, with delayed and lower $C_{max}$ occurring at approximately 5.0 hours post dose (FIG. 4). In contrast, CD was slowly absorbed, with median $C_{max}$ occurring at approximately 4.5 hours post dose. No LD concentration was observed before 0.75 hr for IPX066 Test B. Because of tartaric acid (215 mg) in the formulation, IPX066 Test B also has higher LD concentration between 5 and 8 hr when compared to Sinemet® CR. However, the AUC of LD for IPX066 Test B was only 56.5% of that of reference Sinemet® CR.

Pharmacokinetics of IPX066 Test C and Sinemet® CR

Following administration of one IPX066 Test C tablet, only 4 subjects have detectable LD concentration (FIG. 4). This is due to the slow in vitro release profile for the CD/LD core seed.

The data herein demonstrated that delayed dissolution rate decreases the exposure of LD and CD, and addition of TA to LD and CD formulation has higher LD concentration between 5 and 8 hr when compared to Sinemet® CR.

IPX066-B07-01 Formulation A

| Ingredients | % (w/w) | Amount (mg) |
|---|---|---|
| Carbidopa | 11.24 | 53.98 |
| Levodopa | 41.65 | 200.0 |
| Microcrystalline cellulose (Avicel PH101) | 22.67 | 108.85 |
| HPMC | 3.98 | 19.10 |
| Eudragit ® L100 | 1.70 | 8.17 |
| Eudragit ® SI00 | 8.51 | 40.85 |
| Triethyl Citrate | 7.13 | 34.26 |
| Talc | 3.04 | 14.58 |
| Ammonia Solution | 0.08 | 0.38 |
| Total | 100.0 | 480.17 |
| Tartaric Acid | 42.27 | 215.0 |
| Microcrystalline cellulose (Avicel PH101) | 10.58 | 53.8 |
| Ethylcellulose | 4.88 | 24.8 |
| HPMC | 1.00 | 5.1 |
| Eudragit ® L100 | 3.48 | 17.7 |
| Eudragit ® SI00 | 17.36 | 88.3 |
| Triethyl Citrate | 14.57 | 74.1 |
| Talc | 5.70 | 29.0 |
| Ammonia Solution | 0.16 | 0.8 |
| Total | 100.0 | 508.6 |

IPX066-B07-01 Formulation B

| Ingredients | % (w/w) | Amount (mg) |
|---|---|---|
| Carbidopa | 12.65 | 53.98 |
| Levodopa | 46.87 | 200.0 |
| Microcrystalline cellulose (Avicel PHI01) | 25.51 | 108.85 |
| Hypromellose, Type 2910 | 4.48 | 19.10 |
| Eudragit ® SI00 | 6.42 | 27.38 |
| Triethyl Citrate | 3.21 | 13.71 |
| Talc | 0.80 | 3.40 |
| Amonia Solution | 0.06 | 0.27 |
| Total | 100.0 | 426.69 |
| Tartaric Acid | 42.38 | 215.0 |
| Microcrystalline cellulose (Avicel PH101) | 10.61 | 53.8 |
| Ethylcellulose | 4.89 | 24.8 |
| Hypromellose, Type 2910 | 1.01 | 5.1 |
| Eudragit ® SI00 | 26.01 | 131.95 |
| Triethyl Citrate | 13.01 | 65.98 |
| Talc | 1.81 | 9.16 |
| Ammonia Solution | 0.29 | 1.46 |
| Total | 100.0 | 507.25 |

IPX066-B07-01 Formulation C

| Ingredients | % (w/w) | Amount (mg) |
|---|---|---|
| Carbidopa | 8.57 | 53.98 |
| Levodopa | 31.74 | 200.0 |
| Microcrystalline cellulose (Avicel PH-101) | 17.28 | 108.85 |

-continued

| Ingredients | % (w/w) | Amount (mg) |
|---|---|---|
| Hypromellose, Type 2910 | 3.03 | 19.10 |
| Eudragit ® FS 30D | 30.31 | 190.97 |
| Triethyl Citrate | 0.91 | 5.71 |
| Talc | 8.07 | 50.86 |
| Ammonia Solution | 0.10 | 0.63 |
| Total | 100.0 | 630.10 |
| Tartaric Acid | 38.60 | 215.0 |
| Microcrystalline cellulose (Avicel PH-101) | 9.66 | 53.8 |
| Ethylcellulose | 4.45 | 24.8 |
| Hypromellose, Type 2910 | 0.92 | 5.1 |
| Eudragit ® FS 30D | 35.75 | 199.1 |
| Triethyl Citrate | 1.08 | 6.0 |
| Talc | 9.44 | 52.6 |
| Ammonia Solution | 0.11 | 0.6 |
| Total | 100.0 | 557.0 |

Example 4

The data herein shows the bioavailability/pharmacokinetic results of an enteric coated CD/LD formulations, using 50-200 mg of CD-LD with 0-430 mg of tartaric acid, compared to the controlled release version of Sinemet®.

Four formulations of IPX-066-AH1 were evaluated for PK parameters. Information of the study drugs are listed below in Table 7.

Formulation A is a capsule containing IR beads exhibiting a rapid dissolution profile.

Formulation B is a capsule containing ER CD/LD beads and ER TA beads. The ER CD/LD beads were formulated by coating the IR beads with Eudragit® polymers (S100:L100 ratio of 2:1). The ER TA beads were coated with a seal coat and a Eudragit® coat (S100:L100 ratio of 2:1) exhibiting a dissolution profile similar to the CD/LD beads.

Formulation C is a capsule containing ER CD/LD beads and ER TA beads. The ER CD/LD beads were formulated by coating the IR beads with Eudragit® polymers (S100:L100 ratio of 5:1). The ER TA beads were coated with a seal coat and a Eudragit® coat (S100:L100 ratio of 5:1) exhibiting a dissolution profile similar to the CD/LD beads.

Formulation D is similar to formulation B except that the quantity of the TA beads is twice the amount in formulation B.

Formulation E is the reference product, Sinemet® CR 200 mg Tablet.

TABLE 7

IPX066-AH1(A-D)

| Product | | CD-LD Strength (mg) | Enteric Coated pH |
|---|---|---|---|
| Formulation A | EPX066 CD/LD IR Capsule | 50-200 | |
| Formulation B | IPX066 CD/LD Capsule with 215 mg tartaric acid | 50-200 | 6.5 (SL2)[b] |
| Formulation C | IPX066 CD/LD Capsule with 215 mg tartaric acid | 50-200 | 6.5 (SL5)[b] |
| Formulation D | IPX066 CD/LD Capsule with 430 mg tartaric acid | 50-200 | 6.5 (SL2)[b] |
| Formulation E (Reference) | Sinemet ® CR Tablet[α] | 50-200 | — |

[α]Merck & Co., Inc.;
[b]SL2: Eudragit ® S100/L100 is 2:1; SL5: Eudragit ® S100/L100 is 5:1.

The qualitative and quantitative compositions for these formulations are summarized below in Table 8.

TABLE 8

Qualitative and Quantitative Composition of Formulation

| | Formulation | | | |
|---|---|---|---|---|
| | A | B | C | D |
| | mg/capsule | | | |
| Ingredients | Component I | Component II | Component IV | Component II |
| Carbidopa, USP | 27 | 27 | 27 | 27 |
| Levodopa, USP | 100 | 100 | 100 | 100 |
| Microcrystalline Cellulose, NF (Avicel PH-101) | 18.4 | 18.4 | 18.4 | 18.4 |
| Lactose Monohydrate, NF | 18.4 | 18.4 | 18.4 | 18.4 |
| Sodium Starch Glycolate, NF | 9.2 | 9.2 | 9.2 | 9.2 |
| Sodium Lauryl Sulfate, NF | 9.2 | 9.2 | 9.2 | 9.2 |
| Povidone, USP | 1.84 | 1.85 | 1.85 | 1.85 |
| Talc, USP | 1.95 | 1.95 | 4.2 | 1.95 |
| Methacrylic acid copolymer, Type A, NF (Eudragit ® L100) | | 2.25 | 2.15 | 2.25 |
| Methacrylic acid Copolymer, Type B, NF (Eudragit ® S100) | | 4.55 | 10.75 | 4.55 |
| Triethyl Citrate, NF | — | 1.95 | 9.00 | 1.95 |
| IN NH$_4$OH solution | — | — | 0.1 | — |

TABLE 8-continued

Qualitative and Quantitative Composition of Formulation

| | | | | |
|---|---|---|---|---|
| Purified Water, USP | — | — | N/A* | — |
| Acetone, NF | N/A* | N/A* | — | N/A* |
| Isopropyl Alcohol, USP | N/A* | N/A* | — | N/A* |

| | Component III | Component V | Component III |
|---|---|---|---|
| Tartaric acid, NF | — | 107.5 | 107.5 | 215 |
| Microcrystalline Cellulose, NF (Avicel PH-101) | | 26.95 | 26.9 | 53.9 |
| Ethylcellulose, NF (Ethocel Standard-10FP Premium) | | 11.2 | 11.3 | 22.4 |
| Hypromellose, USP Type2910 (Pharmacoat 606, 6 cps) | | 20.35 | 20.25 | 40.7 |
| Methacrylic acid copolymer, Type A, NF (Eudragit® L100) | | 9.75 | 6.1 | 19.5 |
| Methacrylic acid Copolymer, Type B, NF (Eudragit® S100) | | 19.3 | 30.35 | 38.6 |
| Triethyl Citrate, NF | — | 8.3 | 25.55 | 16.6 |
| Talc, USP | — | 5.2 | 10.3 | 10.4 |
| 1N NH$_4$OH | — | — | 0.3 | — |
| Purified Water, USP | — | — | N/A* | — |
| Acetone, NF | N/A* | N/A* | — | N/A* |
| Isopropyl Alcohol, USP | N/A* | N/A* | — | N/A* |
| Hard Gelatin Capsule | 1 unit | 1 unit | 1 unit | 1 unit |
| Total Capsule Fill Weight | 184.97 | 403.3 | 448.4 | 611.85 |

*evaporated in drying process

Manufacture of IPX066-AH1 Formulations
Four Formulations of IPX066-AH1
Manufacture of Component 1—CD-LD Fast Release Beads Carbidopa, levodopa, and microcrystalline cellulose, lactose monohydrate, sodium starch glycolate, sodium lauryl sulfate, and povidone were blended and charged in a high shear granulator and granulated with purified water. The granulated wet mass was extruded in an extruder with 1.0 mm hole size screen. The extrudate was charged and spheronized in a spheronizer equipped with 3 mm crosshatch disc. The spheres obtained from the spheronizer were dried in and the drug-loaded pellets were screened with 16, 18 and 25 mesh screens. The pellets retained on 18 and 25 mesh screens were collected. The final blend was prepared by blending the screened CD/LD pellets with talc.

Manufacture of Component II—CD-LD Fast Release Beads Coated with Eudragit® S100:L100 (2:1)

CD/LD core seeds (also referred to as pellets) were prepared as Component I seeds except that there was no final blend with Talc. The enteric coating solution was prepared by dissolving Eudragit® S100 and Eudragit® L100 at the weight ratio of 2:1 and triethyl citrate in isopropyl alcohol and acetone solution. Talc was then dispersed into the polymer solution and mixed continuously throughout the coating process. The CD/LD pellets were spray coated using the coating dispersion in a coater. The coated pellets were dried and then screened through a 16 mesh screen. The final blend was prepared by blending the screened CD/LD pellets with talc.

Manufacture of Component III—Tartaric Acid Fast Release Beads Coated with Eudragit® S100:L100 (2:1)

Tartaric acid was passed through a 20 mesh screen. Screened tartaric acid and microcrystalline cellulose was charged in a high shear mixer and granulated with purified water. The wet mass was extruded in an extruder with 1.0 mm hole size screen. The extrudate was charged and spheronized in a spheronizer equipped with a 3 mm cross hatch disc and the resulting pellets dried overnight in an oven at 60±10° C. The dried pellets were passed through 16, 18 and 25 mesh screens and the pellets retained on 18 and 25 mesh screens were collected.

A seal coat solution was prepared by dissolving hypromellose (Pharmacoat 606) and ethylcellulose in alcoholic solution. The seal coat solution was applied to the tartaric acid pellets in a coater. The pellets were dried and the dried pellets passed through a 14 mesh screen.

An additional seal coat was produced by dissolving hypromellose (Pharmacoat 606) in alcoholic solution. The seal coat solution was applied to the tartaric acid pellet coater, and then the pellets were dried in GPCG-1. The dried pellets were passed through a 14 mesh screen.

An enteric coating solution was prepared by dissolving Eudragit® S100 and Eudragit® L100 at the weight ratio of 2:1 and triethyl citrate in isopropyl alcohol and acetone solution. Mix until dissolved. Talc was dispersed into the polymer solution and mixed continuously throughout the coating process. The screened tartaric acid pellets were charged in a coater and spray coated with the enteric coating dispersion. The coated seeds were dried, and the dried, coated pellets screened through a 14 mesh screen. The final blend was prepared by blending the screened pellets and talc.

Manufacture of Component IV—CD-LD Fast Release Beads Coated with Eudragit® S100:L100 (5:1)

Method of manufacture for this component is the same as those of the component II beads, except that the preparation of the enteric coating dispersion was changed. Specifically, the enteric coating dispersion is prepared by charging the required amount of a first portion of purified water in a stainless steel container, and to which while stirring, Methacrylic Acid Copolymer, Type A, NF were charged and dispersed, thereby making a dispersion. The required amount of 1N NH$_4$OH solution was added drop wise to the dispersion.

A required amount of a second portion of purified water in a separate stainless steel container was charged. While stirring, Methacrylic Acid Copolymer, Type B, NF were charged and dispersed. Then a required amount of 1N NH₄OH solution was added drop wise to the dispersion.

A required amount of a third portion of purified water was charged in a separate stainless steel container. Triethyl citrate was charged and dissolved and talc was added to the solution.

The first dispersion above was added and mixed to the second dispersion and to which was then added the third dispersion above. The mixed solutions were screened through 140 mesh screen.

Manufacture of Component V—TA Fast Release Beads Coated with Eudragit® S100:L100 (5:1)

Method of manufacture for component V beads is the same as those of the component III beads, except that the preparation of the enteric coating dispersion was changed.

Specifically the enteric coating dispersion was prepared by charging the required amount of a first portion of purified water in a stainless steel container and, to which, while stirring, Methacrylic Acid Copolymer, Type A, and NF were charged and dispersed to yield a dispersion; then the required amount of 1N NH₄OH solution was added drop wise to the above dispersion.

In a separate stainless steel container, the required amount of the second portion of purified water was charged and while stirring, Methacrylic Acid Copolymer, Type B, and NF were charge and dispersed to yield a dispersion; then the required amount of 1N NH₄OH solution was added to the above dispersion.

In a separate stainless steel container, the required amount of the third portion of purified water was charged and to which triethyl citrate was added and charged; then talc was added to the above solution.

The first dispersion above was added and mixed to the second dispersion and to which was then added the third dispersion above. The mixed solutions were screened through 140 mesh screen.

Manufacture of the IPX066 Capsules

The required amounts of the component beads were filled into hard gelatin capsules according to the specified fill weights in the Table 9 below. The in-process fill weight is controlled at target ±10% of the target weights according to Table 9.

TABLE 9

Target Fill Weights of IPX066 Capsule Test Formulations

| Components | IPX066-AH1(A) mg/capsule | IPX066-AH1(B) mg/capsule | IPX066-AH1(C) mg/capsule | IPX066-AH1(D) mg/capsule |
|---|---|---|---|---|
| Component I Beads | 184.97 | — | — | — |
| Component II Beads | — | 194.75 | — | 194.75 |
| Component III Beads | — | 208.55 | — | 417.1 |
| Component IV Beads | — | — | 210.25 | — |
| Component V Beads | — | — | 238.55 | — |
| Total Capsule Fill weight | 403.3 | 448.8 | 611.85 | |

Pharmacokinetics Result for Biostudy IPX066-AH1

The pharmacokinetics parameters of CD and LD for four tested formulations compared to Sinemet® CR after oral administration are summarized in Table 10.

TABLE 10

Mean ratio of Ln-transformed $C_{max}$ AUC of Levodopa and Carbidopa

| | Parameter | Test/Ref | Ratio (%) |
|---|---|---|---|
| LD | Ln($C_{max}$) | A/E | 192.54 |
| | Ln($C_{max}$) | B/E | 127.05 |
| | Ln($C_{max}$) | C/E | 123.22 |
| | Ln($C_{max}$) | D/E | 111.99 |
| | Ln(AUC) | A/E | 126.53 |
| | Ln(AUC) | B/E | 115.03 |
| | Ln(AUC) | C/E | 127.15 |
| | Ln(AUC) | D/E | 108.74 |
| CD | Ln($C_{max}$) | A/E | 144.73 |
| | Ln($C_{max}$) | B/E | 88.97 |
| | Ln($C_{max}$) | C/E | 124.35 |
| | Ln($C_{max}$) | D/E | 81.06 |
| | Ln(AUC) | A/E | 161.73 |
| | Ln(AUC) | B/E | 91.24 |
| | Ln(AUC) | C/E | 139.79 |
| | Ln(AUC) | D/E | 88.03 |

Results and Discussion:

The data herein demonstrated that formulation A, with the inclusion of water soluble filler such as lactose and a surfactant such as sodium lauryl sulfate, exhibits a rapid LD absorption with a $T_{max}$ of 30 min. The PK profiles of Formulation B and D are desirable. Both formulations exhibit a significantly higher LD plasma concentration at 6 hours post-dose relative to the Sinemet® CR Tablet. The absorption of LD from formulation B and D are also similar as indicated by a relative AUC of 115% and 109%, respectively. Since the PK profiles of formulation B and D are similar, formulation D with double the quantity of TA beads does not offer any additional benefit over formulation B. Formulation C, with coating consisting of Eudragit® S100: L100 ratio of 5:1, exhibits a PK profile suggesting a faster in-vivo release relative to formulation C and D. This is further supported by an AUC of 127% relative to Sinemet® CR Tablet indicating LD was rapidly released and absorbed in the upper GI tract.

Example 5

The data herein shows the bioavailability/pharmacokinetic results of an enteric coated CD/LD formulations, using 50-300 mg of CD-LD with 0-270 mg of tartaric acid compared to the controlled release version of Sinemet®. Information of study drugs are listed below in Table 11.

IPX066-AH2 Formulation A (IPX066-AH2(A)) is a capsule containing 5 different component beads. Component I is an immediate-release CD/LD bead type. Component II is an ER CD/LD bead type with a fast ER release profile. Component III is an ER CD/LD bead type with a slow ER release profile. Component IV is a TA bead type with a release profile similar to those of Component II. Component V is a TA bead type with a release profile similar to those of Component III.

IPX066-AH2 Formulation B (IPX066-AH2(B)) is a capsule containing ER CD/LD beads formulated with Cremophor RH40 and Poloxamer 188. TA is not included in the formulation.

IPX066-AH2 Formulation C (IPX066-AH2(C)) is a capsule containing ER CD/LD beads formulated with Cremophor RH40 and Poloxamer 188, and TA.

IPX066-AH2 Formulation D (IPX066-AH2(D)) is a capsule containing ER CD/LD beads formulated with TA. The capsule does not contain Cremophor RH40 nor Poloxamer 188.

The reference product is Sinemet® CR Tablet 200 mg.

TABLE 11

IPX066-AH2

| | Product | CD-LD Strength (mg) | Enteric Coated pH |
|---|---|---|---|
| A | IPX066 CD/LD Combo Capsule with 270 mg tartaric acid (IR + fast release core + slow release core) | 75-300 | 6.5 (SL2) for fast and slow release core |
| B | IPX066 CD/LD Capsule with surfactants | 50-200 | 6.5 (SL2) |
| C | IPX066 CD/LD/tartaric acid Capsule with 215 mg tartaric acid and surfactants | 50-200 | 6.5 (SL2) |
| D | IPX066 CD/LD/tartaric acid Capsule with 215 mg tartaric acid | 50-200 | 6.5 (SL2) |
| E | Sinemet ® CR Tablet[α] | 50-200 | — |

[α]Merck & Co., Inc.

The qualitative and quantitative compositions for these formulations are summarized below in Table 12 and Table 13.

TABLE 12

Formulation A (IPX066-AH2(A))

| Ingredients | Formulation A mg/capsule |
|---|---|
| Component I | |
| Carbidopa USP | 6.75 |
| Levodopa USP | 25 |
| Microcrystalline Cellulose NF | 4.6 |
| Lactose Monohydrate NF | 4.5 |
| Sodium Starch Glycolate NF | 2.3 |
| Sodium Lauryl Sulfate NF | 2.3 |
| Povidone USP | 0.46 |
| Talc USP | 0.23 |
| Purified Water, USP | N/A* |
| Component II | |
| Carbidopa USP | 6.75 |
| Levodopa USP | 25 |
| Microcrystalline Cellulose NF | 4.6 |
| Lactose Monohydrate NF | 4.6 |
| Sodium Starch Glycolate NF | 2.3 |
| Sodium Lauryl Sulfate NF | 2.3 |
| Povidone USP | 0.46 |
| Methacrylic acid copolymer, Type A NF (Eudragit ® LI00) | 0.55 |
| Methacrylic acid Copolymer, Type B NF (Eudragit ® SI00) | 1.15 |
| Triethyl Citrate NF | 0.48 |
| Talc USP | 0.49 |
| Acetone, NF | N/A* |
| Isopropyl Alcohol, USP | N/A* |
| Purified Water, USP | N/A* |
| Component III | |
| Carbidopa USP | 26.99 |
| Levodopa USP | 100 |
| Microcrystalline Cellulose NF | 54.42 |
| Methacrylic acid copolymer, Type A NF (Eudragit ® LI00) | 2.18 |
| Methacrylic acid Copolymer, Type B NF (Eudragit ® SI00) | 4.5 |
| Triethyl Citrate NF | 1.91 |
| Talc USP | 1.91 |

TABLE 12-continued

Formulation A (IPX066-AH2(A))

| Ingredients | Formulation A mg/capsule |
|---|---|
| Acetone, NF | N/A* |
| Isopropyl Alcohol, USP | N/A* |
| Purified Water, USP | N/A* |
| Component IV | |
| Tartaric acid NF | 27 |
| Microcrystalline Cellulose NF | 6.79 |
| Ethylcellulose NF | 2.81 |
| Hypromellose, Type2910 USP | 5.01 |
| Methacrylic acid copolymer, Type A NF (Eudragit ® LI00) | 2.44 |
| Methacrylic acid Copolymer, Type B NF (Eudragit ® S100) | 4.84 |
| Triethyl Citrate NF | 2.08 |
| Talc USP | 1.31 |
| Acetone, NF | N/A* |
| Isopropyl Alcohol, USP | N/A* |
| Purified Water, USP | N/A* |
| Component V | |
| Tartaric acid NF | 107.5 |
| Microcrystalline Cellulose NF | 26.85 |
| Ethylcellulose NF | 12.38 |
| Hypromellose Type 2910 USP | 2.63 |
| Methacrylic acid copolymer, Type A NF (Eudragit ® LI00) | 8.62 |
| Methacrylic acid Copolymer, Type B NF (Eudragit ® SI00) | 17.5 |
| Triethyl Citrate NF | 7.45 |
| Talc USP | 4.69 |
| Acetone, NF | N/A* |
| Isopropyl Alcohol, USP | N/A* |
| Purified Water, USP | N/A* |
| Hard Gelatin Capsule | 1 unit |
| Total Capsule Fill weight | 526.63 |

*evaporated in drying process

TABLE 13

Formulations B, C and D (IPX066-AH2(B), IPX066-AH2(C), IPX066-AH2(D))

| | Formulation | | |
|---|---|---|---|
| Ingredients | B mg/capsule | C mg/capsule | D mg/capsule |
| Carbidopa USP | 26.99 | 26.99 | 26.99 |
| Levodopa USP | 100 | 100 | 100 |
| Microcrystalline Cellulose, NF | 118.75 | 65.00 | 30.00 |
| Lactose Monohydrate NF | 53.75 | — | — |
| Mannitol, USP | — | — | 50.00 |
| Povidone, USP | 17.35 | — | — |
| Talc, USP | 23.99 | 11.11 | 9.97 |
| Methacrylic acid copolymer, Type A, NF (Eudragit ® L100) | 48.98 | 20.13 | 18.09 |
| Methacrylic acid Copolymer, Type B, NF (Eudragit ® SI00) | 98.19 | 40.35 | 36.17 |
| Triethyl Citrate, NF | 42.18 | 17.32 | 15.55 |
| Poloxamer 188, NF | 33.5 | 33.5 | — |
| Polyoxyl 40 Hydrogenated Castor Oil, NF (Cremophor RH 40) | 17.5 | 17.5 | |
| Tartaric acid, NF | — | 107.5 | 107.5 |
| Hypromellose, USP Type 2910 | | 52.58 | 47.18 |
| Acetone, NF | N/A* | N/A* | N/A* |

TABLE 13-continued

Formulations B, C and D (IPX066-AH2(B), IPX066-AH2(C), IPX066-AH2(D))

| | Formulation | | |
|---|---|---|---|
| Ingredients | B mg/capsule | C mg/capsule | D mg/capsule |
| Isopropyl Alcohol, USP | N/A* | N/A* | N/A* |
| Purified Water, USP | N/A* | N/A* | N/A* |
| Hard Gelatin Capsule | 1 unit | 1 unit | 1 unit |
| Total Capsule Fill Weight | 581.18 | 491.98 | 441.45 |

*evaporated in drying process

Manufacture of Formulation A (IPX066-AH2 (A))
Manufacture of Component Bead I—CD/LD Fast Release Beads Method of manufacture for this component beads is the same as to that for component I beads in IPX066-AH1, as discussed in Example 4 above.

Manufacture of Component II—CD-LD Fast Release Beads Coated with Eudragit® S100:L100 (2:1)

Method of manufacture for this component beads is the same as that for component II beads in IPX066-AH1, as discussed in Example 4 above.

Manufacture of Component III—CD-LD Slow Release Beads Coated with Eudragit® S100:L100 (2:1)

Method of manufacture for this component beads is the same as that for enteric coated CD-LD beads in formulation A tested in IPX066-B06-02, as discussed in Example 2 above.

Manufacture of Component IV—TA Fast Release Beads Coated with Eudragit® S100:L100 (2:1)

Method of manufacture for this component beads is the same as that of component III beads in biostudy IPX066-AH1, as discussed in Example 4 above.

Manufacture of Component V—TA Slow Release Beads Coated with Eudragit® S100:L100 (2:1)

Method of manufacture for this component beads is the same as that for enteric coated tartaric acid beads in formulation A tested in IPX066-B06-02 as discussed in Example 2 above.

Manufacture of the IPX066 Capsules for Formulation A

The required amounts of the component beads were filled into hard gelatin capsules according to the specified target fill weights ±10%.

TABLE 14

Target Fill Weights of IPX066 Capsule Test Formulations

| Components | IPX066-AH2(A) mg/capsule |
|---|---|
| Component I Beads | 46.2 |
| Component II Beads | 48.7 |
| Component III Beads | 191.9 |
| Component IV Beads | 52.1 |
| Component V Beads | 187.7 |
| Total Capsule Fill weight | 526.6 |

Manufacture of Test Formulation B (IPX066-AH2(B))

To make formulation B, a suitable amount of ethanol and purified water were mixed and to which Cremophor RH40 was dissolved and charged in a first solution; then povidone was charged and mixed in the solution. A separate granulating fluid was prepared by dissolving the required amount of povidone in the required amount of purified water.

Suitable amounts of carbidopa, levodopa, microcrystalline cellulose, lactose monohydrate and poloxamer were charged into a suitable granulator and mixed until a uniform powder is formed.

The mixed powder was granulated by adding the first solution above followed by continued granulation by adding the separate granulating fluid above thereby resulting in a wet mass. The wet mass was extruded through a suitable extruder equipped with a screen size of 1.0 mm. The extrudate was spheronized in a spheronizer at an appropriate speed and the wet extruded beads were dried in a fluidized bed dryer. The dried beads were then passed through a US #16 mesh screen, US #18 mesh screen, US #25 mesh screen and pan. Only the beads that pass through 18 mesh but retained on 25 mesh screen are collected.

The enteric coating dispersion was prepared by dispensing and mixing a suitable amount of acetone and isopropyl alcohol and while mixing the solution, triethyl citrate was charged and dissolved in the solution. The mixing was continued until the material was fully dissolved. While mixing, Methacrylic Acid Copolymer, Type A, NF was charged to the solution. The solution was mixed until the material was fully dissolved then again while mixing, Methacrylic Acid Copolymer, Type B, NF was charged to the solution. Mixing continued until the material was fully dissolved. While mixing, talc was charged and dispersed in the solution. Mixing continued throughout the coating process.

The collected beads above were charged into a suitable fluidized-bed coater equipped with a Wurster insert and were spray coated using the enteric coating dispersion above. The coated beads were dried, and the dried beads were passed through a US #14 mesh screen. The resulting screened material was charged and a suitable amount of talc was added to it in a suitable blender and mixed until uniform.

Manufacture of Test Formulation C (IPX066-AH2(C))

A suitable amount of ethanol and purified water was dispensed and mixed in a stainless steel container to which was charged and dissolved a suitable amount of Cremophor RH40 resulting in a granulating solution.

A suitable amount of carbidopa, levodopa, tartaric acid, microcrystalline cellulose, and poloxamer was charged into a suitable granulator and mixed until uniform. The mixed powder was granulated with the granulating solution above thus creating a wet mass. The wet mass was extruded through a suitable extruder equipped with a screen size of 1.0 mm and the extrudate was spheronized in a suitable spheronizer at an appropriate speed.

The wet extruded beads were dried in the fluidized bed dryer. The LOD was measured using a Moisture Analyzer and the drying process was stopped when the LOD value was not more than a target value 3%. The dried beads were then passed through a US #16 mesh screen, US #18 mesh screen, US #25 mesh screen and pan. Only the beads retained on 18 mesh and on 25 mesh screen were collected and blended.

The seal coat solution was prepared as follows. An ethanol solution was prepared by mixing the required amount of alcohol, USP and purified water in a stainless steel container. A suitable amount hypromellose was charged and dissolved in the ethanol solution.

The collected beads retained on 18 mesh and on 25 mesh screen were charged into a fluidized bed coater equipped with a Wurster insert and spray coated using the seal coat solution prepared above. The coated beads were dried in the fluidized bed and the dried beads were passed through a US #14 mesh screen. The beads that pass through the screen were collected.

The enteric coating dispersion was prepared as follows. A suitable amount of Methacrylic Acid Copolymer, Type A, NF, Methacrylic Acid Copolymer, Type B, NF, triethyl citrate and talc were dispensed. A suitable amount of acetone and isopropyl alcohol were mixed well and during the mixing, triethyl citrate was charged and mixed into the solution. Methacrylic Acid Copolymer, Type A, NF was further charged into the solution. Mixing continued until the material was fully dissolved. Methacrylic Acid Copolymer, Type B, NF was additionally charged into the solution. Mixing continued until the material was fully dissolved. Talc was then charged and dispersed in the solution. Mixing occurred throughout the process.

The collected beads were coated with the enteric coating dispersion as follows. The collected beads were charged in a suitable fluidized-bed coater equipped with a Wurster insert and spray coated with the enteric coating dispersion above. The coated beads were then dried and the dried beads passed through a US #14 mesh screen. The screened material was mixed and charged with a suitable amount of talc in a blender.

Manufacture of Test Formulation D (IPX066-AH2(D))

A granulating solution was prepared by dissolving polyoxyl in a solution of ethanol and purified water.

A suitable amount of carbidopa, levodopa, screened tartaric acid, microcrystalline cellulose, lactose monohydrate and poloxamer were charged and mixed in a granulator. The mixed material was granulated with the granulating solution thereby creating a wet mass. The wet mass was extruded through a suitable extruder equipped with a screen size of 1.0 mm. The resulting extrudates were spheronized in a suitable spheronizer. The wet extruded beads were dried in a fluidized bed dryer and the LOD was measuring using a Moisture Analyzer. The drying process was stopped when the LOD value is not more than a target value 3%.

The dried beads were passed through a US #16 mesh screen, US #18 mesh screen, US #25 mesh screen and pan. Only the beads retained on 18 mesh and on 25 mesh screen were collected and retained.

The dried beads were coated with a seal coat. The seal coat may be prepared as follows. An ethanol solution was prepared by mixing the required amount of Alcohol, USP and purified water in a stainless steel container to which a suitable amount hypromellose was charged. The dried beads were charged into a fluidized bed coater equipped with a Wurster insert and spray coated using the seal coat solution. The coated beads were then dried in a fluidized bed and the dried coated beads passed through a US #14 mesh screen. The beads that passed through the screen were collected.

The collected beads were coated with an enteric coating dispersion. The enteric coating dispersion was prepared as follows. A suitable amount of Methacrylic Acid Copolymer, Type A, NF, Methacrylic Acid Copolymer, Type B, NF, triethyl citrate and talc was dispersed. A suitable amount of acetone and isopropyl alcohol was mixed well. During the mixing, triethyl citrate was charged and dissolved in the acetone and isopropyl alcohol solution. Then while mixing, Methacrylic Acid Copolymer, Type A, and NF were charged into the solution. Mixing continued until the material was fully dissolved. During the mixing, Methacrylic Acid Copolymer, Type B, and NF were charged into the solution. Mixing continued until the material was fully dissolved. Then talc was charged and dissolved in the solution. Mixing continued throughout the coating process.

The seal coated beads were charged into a suitable fluidized-bed coater equipped with a Wurster insert and spray coated using the enteric coating dispersion. The resulting coated beads were dried and the dried beads were passed through a US #14 mesh screen. The screened material were charged and mixed with a suitable amount of talc in a blender until uniform.

Pharmacokinetics Result for Biostudy IPX066-AH2

The Pharmacokinetics parameters of CD and LD for four tested formulations compared to Sinemet® CR after oral administration are summarized in Table 15.

TABLE 15

Mean ratio of Ln-transformed $C_{max}$, AUC of Levodopa and Carbidopa

|    | Parameter | Test/Ref | Ratio (%) |
|----|-----------|----------|-----------|
| LD | $Ln(C_{max})$ | A/E | 80.73 |
|    | $Ln(C_{max})$ | B/E | 16.19 |
|    | $Ln(C_{max})$ | C/E | 18.15 |
|    | $Ln(C_{max})$ | D/E | 16.55 |
|    | Ln(AUC)   | A/E | 108.65 |
|    | Ln(AUC)   | B/E | 10.54 |
|    | Ln(AUC)   | C/E | 15.08 |
|    | Ln(AUC)   | D/E | 15.79 |
| CD | $Ln(C_{max})$ | A/E | 80.12 |
|    | $Ln(C_{max})$ | B/E | 7.03 |
|    | $Ln(C_{max})$ | C/E | 13.85 |
|    | $Ln(C_{max})$ | D/E | 14.41 |
|    | Ln(AUC)   | A/E | 94.93 |
|    | Ln(AUC)   | B/E | 2.69 |
|    | Ln(AUC)   | C/E | 12.54 |
|    | Ln(AUC)   | D/E | 11.06 |

Results and Discussion

The data herein demonstrated that formulation A achieved a desirable in vivo plasma concentration profile. By combining two components of tartaric acid beads (with enteric coating on either fast or slow release core) with three components of CD/LD drug seeds/beads (instant release portion, and enteric coated portion with coating on either fast or slow release core), formulation A showed a significantly flatter plasma concentration profile with a lower $C_{max}$ (80.7%) and comparable AUC (109%) relative to the reference drug Sinemet® CR.

A PK simulation study was conducted to calculate the peak to trough plasma concentration (PT) ratio assuming a three times daily (every 6 hours) dosing regimen. The PT ratio is defined on steady state 18 hours post-dose plasma concentration. The simulation results are summarized in Table 16, showing that formulation A has a significantly lower, 1.7, PT ratio relative to Sinemet® CR, 3.4.

The addition of surfactants in formulation significantly decreased LD bioavailability. Moreover, it is more advantageous to have separate drug and tartaric acid seeds in formulation, and the incorporation of tartaric acid into same drug seeds significantly decreased LD bioavailability.

TABLE 16

Simulation of Steady State Plasma Concentration, AUC, and Peak-to-trough Concentration Ratio

| Formulation | CD-LD Dose (mg) | Css, max | Css, 18 hr | Peak to Trough Plasma Conc ratio |
|---|---|---|---|---|
| A (IPX066-AH2(A)) | 75-300 | 1030 | 591 | 1.7 |
| E (reference) | 50-200 | 1212 | 349 | 3.4 |

Example 6

Formulation with separate CD/LD containing surfactant seeds and tartaric acid seeds for IPX-066 was evaluated for PK parameters.

IPX066-AH3

Information of study drugs are listed below in Table 17. Formulation A (IPX066-AH3(A)) is a capsule containing ER CD/LD beads formulated with Cremophor RH40 and Poloxamer 188 and ER TA beads with a similar dissolution profile.

TABLE 17

IPX066-AH3

| | Product | CD-LD Strength (mg) | Enteric Coated pH |
|---|---|---|---|
| A (IPX066-AH3(A)) | IPX066 CD/LD containing surfactant Capsule with 215 mg tartaric acid | 50-200 | 6.5 (SL2) |
| B | Sinemet ® CR Tablet | 50-200 | — |

The qualitative and quantitative compositions for these formulations are summarized below in Table 18.

TABLE 18

Qualitative and Quantitative Composition of Test Formulations

| Ingredients | Formulation A (IPX066-AH3(A)) mg/capsule |
|---|---|
| Bead I | |
| Carbidopa, USP | 17.99 |
| Levodopa, USP | 66.67 |
| Microcrystalline Cellulose, NF (Avicel PH-101) | 79.17 |
| Lactose Monohydrate, NF | 35.83 |
| Poloxamer 188, NF (Lutrol F-68, NF) | 22.33 |
| Polyoxyl 40 Hydrogenated Castor Oil, NF (Cremophor RH 40) | 11.67 |
| Povidone, USP | 11.57 |
| Methacrylic acid copolymer, Type A, NF (Eudragit ® L100) | 32.65 |
| Methacrylic acid Copolymer, Type B, NF (Eudragit ® SI00) | 65.46 |
| Triethyl Citrate, NF | 28.12 |
| Talc, USP | 15.99 |
| Acetone, NF | N/A* |
| Isopropyl Alcohol, USP | N/A* |
| Purified Water, USP | N/A* |
| Bead II | |
| Tartaric acid, NF | 71.67 |
| Microcrystalline Cellulose, NF (Avicel PH-101) | 17.93 |
| Ethylcellulose, NF (Ethocel Standard-10FP Premium) | 7.53 |
| Hypromellose, USP Type2910 (Pharmacoat 606, 6 cps) | 13.50 |
| Methacrylic acid copolymer, Type A, NF (Eudragit ® LI00) | 14.77 |
| Methacrylic acid Copolymer, Type B, NF (Eudragit ® SI00) | 29.50 |
| Triethyl Citrate, NF | 12.63 |
| Talc, USP | 7.20 |
| Acetone, NF | N/A* |
| Isopropyl Alcohol, USP | N/A* |
| Purified Water, USP | N/A* |
| Hard Gelatin Capsule | 1 unit |
| Total weight | 562.18 |

Manufacture of Test Formulation

Manufacture of Component Bead I—CD/LD Beads

Method of manufacture for this component beads is the same as to that for formulation B of IPX066-AH2, as discussed above in Example 5.

Manufacture of Component Bead II—TA Beads

Method of manufacture for this component beads is the same as that of component III beads in IPX066-AH1, except the content for enteric coating is higher in formulation, as discussed in Example 4 above.

Pharmacokinetics Result for IPX066-AH3:

The Pharmacokinetics parameters of CD and LD for tested formulations compared to Sinemet® CR after oral administration are summarized in Table 19.

TABLE 19

Mean ratio of Ln-transformed $C_{max}$, AUC of Levodopa and Carbidopa

| | Parameter | Test/Ref | Ratio (%) |
|---|---|---|---|
| LD | $Ln(C_{max})$ | A/B | 14.89 |
| | $Ln(AUC)$ | A/B | 9.88 |
| CD | $Ln(C_{max})$ | A/B | 4.87 |
| | $Ln(AUC)$ | A/B | 7.11 |

Results and Discussions

The addition of surfactants in formulation significantly decreased LD bioavailability even when the formulation contains separate drug and tartaric acid seeds.

Example 7

Formulations for IPX066-AH4

Four formulations of IPX-066 were evaluated for PK parameters. Information of study drugs are listed below in Table 20.

TABLE 20

IPX066-AH4

| Formulation | CD-LD Dose (mg) | Molar Ratio of TA:LD | Amount of Capsule/dose |
|---|---|---|---|
| A (IPX066-AH4(A)) | 75-300 | 1.4:1 | 2 |
| B (IPX066-AH4(B)) | 90-360 | 1.4:1 | 3 |
| C (IPX066-AH4(C)) | 90-360 | 0.5:1 | 2 |
| D (IPX066-AH4(D)) | 90-360 | 0.75:1 | 2 |
| Sinemet ® CR Tablet[a] | 50-200 | — | — |

[a]Merck & Co., Inc.

These formulations contain CD/LD beads and LD beads with different release characteristics. Similar to formulation A of IPX066-AH2, these beads are coated with Eudragit® L100 and S100 polymer in the ratio of 1:2. The quantities of CD/LD and TA in each of the bead type are shown in Table 20.

Component I is a CD/LD bead type which exhibits an immediate-release dissolution profile.

Component II is a CD/LD bead type which exhibits a faster extended-release dissolution profile.

Component III is a CD/LD bead type which exhibits a slower extended-release dissolution profile.

Component IV is a TA bead type which exhibits a dissolution profile which mimics those of component II.

Component V is a TA bead type which exhibits a dissolution profile which mimics those of component III.

Component VI is a TA bead type which exhibits an intermediate dissolution profile between those of component II and III.

The qualitative and quantitative compositions for these formulations are summarized below in Table 21.

TABLE 21

Qualitative and Quantitative Composition of Formulation

| Ingredients | Formulation A (IPX066-AH4(A)) mg/capsule | Formulation B (IPX066-AH4(B)) mg/capsule | Formulation C (IPX066-AH4(C)) mg/capsule | Formulation D (IPX066-AH4(D)) mg/capsule |
|---|---|---|---|---|
| Component I | | | | |
| Carbidopa USP | 6.75 | 6.48 | 9.72 | 9.72 |
| Levodopa USP | 25 | 24 | 36 | 36 |
| Microcrystalline Cellulose NF | 4.6 | 4.42 | 6.62 | 6.62 |
| Lactose Monohydrate NF | 4.6 | 4.42 | 6.62 | 6.62 |
| Sodium Starch Glycolate NF | 2.3 | 2.21 | 3.31 | 3.31 |
| Sodium Lauryl Sulfate NF | 2.3 | 2.21 | 3.31 | 3.31 |
| Povidone USP | 0.46 | 0.44 | 0.66 | 0.66 |
| Talc USP | 0.23 | 0.22 | 0.33 | 0.33 |
| Purified Water, USP | N/A* | N/A* | N/A* | N/A* |
| Component II | | | | |
| Carbidopa USP | 6.75 | 5.4 | 8.10 | 8.10 |
| Levodopa USP | 25 | 20 | 30 | 30 |
| Microcrystalline Cellulose NF | 4.6 | 3.68 | 5.52 | 5.52 |
| Lactose Monohydrate NF | 4.6 | 3.68 | 5.52 | 5.52 |
| Sodium Starch Glycolate NF | 2.3 | 1.84 | 2.76 | 2.76 |
| Sodium Lauryl Sulfate NF | 2.3 | 1.84 | 2.76 | 2.76 |
| Povidone USP | 0.46 | 0.37 | 0.55 | 0.55 |
| Methacrylic acid copolymer, Type A NF (Eudragit® L100) | 0.56 | 0.45 | 0.67 | 0.67 |
| Methacrylic acid Copolymer, Type B NF (Eudragit® S100) | 1.14 | 0.91 | 1.36 | 1.36 |
| Triethyl Citrate NF | 0.49 | 0.39 | 0.58 | 0.58 |
| Talc USP | 0.49 | 0.39 | 0.58 | 0.58 |
| Acetone, NF | N/A* | N/A* | N/A* | N/A* |
| Isopropyl Alcohol, USP | N/A* | N/A* | N/A* | N/A* |
| Purified Water, USP | N/A* | N/A* | N/A* | N/A* |
| Component III | | | | |
| Carbidopa USP | 26.99 | 20.51 | 30.77 | 30.77 |
| Levodopa USP | 100.00 | 76.00 | 114.00 | 114.00 |
| Microcrystalline Cellulose NF | 54.43 | 41.36 | 62.04 | 62.04 |
| Methacrylic acid copolymer, Type A NF (Eudragit® L100) | 2.19 | 1.67 | 2.50 | 2.50 |
| Methacrylic acid Copolymer, Type B NF (Eudragit® S100) | 4.49 | 3.41 | 5.12 | 5.12 |
| Triethyl Citrate NF | 1.91 | 1.45 | 2.18 | 2.18 |
| Talc USP | 1.92 | 1.46 | 2.18 | 2.18 |
| Acetone, NF | N/A* | N/A* | N/A* | N/A* |
| Isopropyl Alcohol, USP | N/A* | N/A* | N/A* | N/A* |
| Purified Water, USP | N/A* | N/A* | N/A* | N/A* |
| Component IV | | | | |
| Tartaric acid NF | 27.00 | 21.50 | 11.40 | — |
| Microcrystalline Cellulose NF | 6.74 | 5.37 | 2.85 | — |
| Ethylcellulose NF | 2.81 | 2.24 | 1.19 | — |
| Hypromellose, Type 2910 USP | 0.94 | 0.75 | 0.40 | — |
| Methacrylic acid copolymer, Type A NF (Eudragit® L100) | 2.16 | 1.72 | 0.91 | — |
| Methacrylic acid Copolymer, Type B NF (Eudragit® S100) | 4.41 | 3.51 | 1.86 | — |
| Triethyl Citrate NF | 1.87 | 1.49 | 0.79 | — |
| Talc USP | 1.18 | 0.94 | 0.50 | — |
| Acetone, NF | N/A* | N/A* | N/A* | — |
| Isopropyl Alcohol, USP | N/A* | N/A* | N/A* | — |
| Purified Water, USP | N/A* | N/A* | N/A* | — |
| Component V | | | | |
| Tartaric acid NF | 107.50 | 81.70 | 43.4 | — |
| Microcrystalline Cellulose NF | 26.90 | 20.44 | 10.86 | — |
| Ethylcellulose NF | 12.40 | 9.42 | 5.00 | — |
| Hypromellose Type 2910 USP | 2.55 | 1.94 | 1.03 | — |
| Methacrylic acid copolymer, Type A NF (Eudragit® L100) | 8.60 | 6.54 | 3.47 | — |
| Methacrylic acid Copolymer, Type B NF (Eudragit® S100) | 17.55 | 13.34 | 7.09 | — |
| Triethyl Citrate NF | 7.45 | 5.66 | 3.01 | — |
| Talc USP | 4.70 | 3.57 | 1.90 | — |
| Acetone, NF | N/A* | N/A* | N/A* | — |
| Isopropyl Alcohol, USP | N/A* | N/A* | N/A* | — |
| Purified Water, USP | N/A* | N/A* | N/A* | — |

TABLE 21-continued

Qualitative and Quantitative Composition of Formulation

| Ingredients | Formulation A (IPX066-AH4(A)) mg/capsule | Formulation B (IPX066-AH4(B)) mg/capsule | Formulation C (IPX066-AH4(C)) mg/capsule | Formulation D (IPX066-AH4(D)) mg/capsule |
|---|---|---|---|---|
| Component VI | | | | |
| Tartaric acid NF | — | — | — | 82.20 |
| Microcrystalline Cellulose NF | — | — | — | 20.57 |
| Ethylcellulose NF | — | — | — | 9.14 |
| Hypromellose Type 2910 USP | — | — | — | 2.29 |
| Methacrylic acid copolymer, Type A NF (Eudragit ® L100) | | | | 6.58 |
| Methacrylic acid Copolymer, Type B NF (Eudragit ® S100) | | | | 13.42 |
| Triethyl Citrate NF | — | — | — | 5.70 |
| Talc USP | — | — | — | 3.59 |
| Acetone, NF | N/A* | N/A* | N/A* | N/A* |
| Isopropyl Alcohol, USP | N/A* | N/A* | N/A* | N/A* |
| Purified Water, USP | N/A* | N/A* | N/A* | N/A* |
| Hard Gelatin Capsule | 1 unit | 1 unit | 1 unit | 1 unit |
| Total Capsule Fill weight | 521.62 | 409.34 | 439.41 | 487.25 |

*evaporated in drying process

Manufacture of Test Formulations

Manufacture of Component I—CD-LD Fast Release Beads

Method of manufacture for this component beads is the same as to that for component I beads for formulation A in IPX066-AH2, as discussed in Example 5 above.

Manufacture of Component II—CD-LD Fast Release Beads Coated with Eudragit® S100:L100 (2:1)

Method of manufacture for this component beads is the same as to that for component II beads for formulation A in IPX066-AH2, as discussed in Example 5 above.

Manufacture of Component III—CD-LD Slow Release Beads Coated with Eudragit® S100:L100 (2:1)

Method of manufacture for this component beads is the same as to that for component III beads for formulation A in IPX066-AH2, as discussed in Example 5 above.

Manufacture of Component IV—TA Fast Release Beads Coated with Eudragit® S100:L100 (2:1)

Method of manufacture for this component beads is the same as to that for component IV beads for formulation A in IPX066-AH2, as discussed in Example 5 above, except no additional seal coat was introduced between seal coating layer and enteric coating layer.

Manufacture of Component V—TA Slow Release Beads Coated with Eudragit® S100:L100 (2:1)

Method of manufacture for this component beads is the same as to that for component V beads for formulation A in IPX066-AH2, as discussed in Example 5 above.

Manufacture of Component VI—TA Medium Release Beads Coated with Eudragit® S100:L100 (2:1)

Method of manufacture for this component beads is the same as to that for component V beads except the content ratio of ethylcellulose/hypromellose in seal coating is 4/1 instead of 5/1.

Manufacture of the IPX066 Capsules

The required amounts of the component beads were filled into hard gelatin capsules according to the specified fill weights in the Table 22 below. The in-process fill weight is controlled at target ±10% of the target weights according to Table 22.

TABLE 22

Target Fill Weights of IPX066 Capsule Test Formulations

| | Formulation Code | | | |
|---|---|---|---|---|
| Components | IPX066-AH4(A) mg/capsule | IPX066-AH4(B) mg/capsule | IPX066-AH4(C) mg/capsule | IPX066-AH4(D) mg/capsule |
| Component I Beads | 46.24 | 44.4 | 66.57 | 66.57 |
| Component II Beads | 48.69 | 38.95 | 58.40 | 58.40 |
| Component III Beads | 191.93 | 145.86 | 218.79 | 218.79 |
| Component IV Beads | 47.11 | 37.52 | 19.89 | |
| Component V Beads | 187.65 | 142.61 | 75.76 | |
| Component VI Beads | — | — | — | 143.49 |
| Total Capsule Fill weight | 521.62 | 409.34 | 439.41 | 487.25 |

Pharmacokinetics Result for IPX066-AH4

The Pharmacokinetics parameters of CD and LD for four tested formulations compared to Sinemet® CR after oral administration are summarized in Table 23.

TABLE 23

Mean Ratio of Ln-transformed $C_{max}$, AUC of Levodopa and Carbidopa

|    | Parameter | Test/Ref | Ratio (%) |
|----|-----------|----------|-----------|
| LD | Ln($C_{max}$) | A/E | 92.29 |
|    | Ln($C_{max}$) | B/E | 119.02 |
|    | Ln($C_{max}$) | C/E | 132.54 |
|    | Ln($C_{max}$) | D/E | 133.78 |
|    | Ln(AUC) | A/E | 105.14 |
|    | Ln(AUC) | B/E | 136.15 |
|    | Ln(AUC) | C/E | 143.73 |
|    | Ln(AUC) | D/E | 154.34 |
| CD | Ln($C_{max}$) | A/E | 92.76 |
|    | Ln($C_{max}$) | B/E | 116.37 |
|    | Ln($C_{max}$) | C/E | 126.66 |
|    | Ln($C_{max}$) | D/E | 135.66 |
|    | Ln(AUC) | A/E | 111.12 |
|    | Ln(AUC) | B/E | 149.98 |
|    | Ln(AUC) | C/E | 145.70 |
|    | Ln(AUC) | D/E | 164.13 |

Results and Discussion

Test formulation A (IPX066-AH4(A)) showed a consistent in vivo plasma concentration profile as those of formulation A (IPX066-AH2(A)) in IPX066-AH2. Formulation IPX066-AH2(A) and IPX066-AH4(A) differs only in the filler used, i.e. lactose in IPX066-AH2(A) and mannitol in IPX066-AH4(A). The relative AUC (relative to Sinemet® CR Tablet) is 109% and 105% for formulation IPX066-AH2(A) and IPX066-AH4(A), respectively. The relative $C_{max}$ (relative to Sinemet® CR Tablet) is 80.7% and 92.3% for formulation IPX066-AH2(A) and IPX066-AH4(A), respectively. Therefore, the in-vivo performance and bioavailability of the formulation is reproducible and consistent.

Based on a simulation study, the steady state peak to trough plasma concentration (PT) ratio was calculated assuming a three times daily, every 6 hours, dosing. The simulated PT ratios, defined as ratio of $C_{max}$ and $C_{ss}$, 18 hours, are summarized in Table 24. The results showed that PT ratio of formulation A (IPX066-AH4(A)), B (IPX066-AH4(B)), C (IPX066-AH4(C)), and D (IPX066-AH4(D)) are 1.8, 2.3, 2.8, and 2.0, respectively. The PT ratio of Sinemet® CR Tablet is 3.9. Therefore, all IPX066 test formulations have a lower PT ratio relative to the reference, Sinemet® CR Tablet.

The data herein also demonstrated the optimum molar ratio of TA:LD to be 0.75, when comparing PT ratio of formulation B, C, and D.

The PK results also indicated that replacing the TA beads of fast and slow release profiles with TA beads with an intermediate release profile in formulation did not change the overall in vivo LD plasma profile significantly, as evidenced by the PT ratio.

TABLE 24

Simulation of Steady State Plasma Concentration, AUC, and Peak-to-trough Concentration Ratio.

| Test Formulation | CD-LD Dose (mg) | TA;LD Molar Ratio | $C_{ss,max}$ | Css, 18 hr | AUCss, 24 | Peak to Trough Plasma Conc ratio |
|---|---|---|---|---|---|---|
| A | 75-300 | 1.4 | 920 | 511 | 13215 | 1.8 |
| B | 90-360 | 1.4 | 1238 | 549 | 17048 | 2.3 |
| C | 90-360 | 0.5 | 1337 | 477 | 18204 | 2.8 |
| D | 90-360 | 0.75 | 1384 | 679 | 19848 | 2.0 |
| E (reference) | 50-200 | 0 | 984 | 254 | 12348 | 3.9 |

Example 8

IPX066-AH5(A) (47.5 mg CD/190 mg LD) was evaluated for PK parameters in a three way cross over PK study using Sinemet® CR (200 mg) as reference. The qualitative and quantitative compositions for this formulation are summarized below.

TABLE 25

Quantitative Composition of Formulation IPX066-AH5(A)

| Ingredients | % | Dosage strength 190 mg mg/capsule |
|---|---|---|
| Carbidopa | 10.21 | 51.29* |
| Levodopa | 37.84 | 190.00 |
| Tartaric acid | 17.63 | 88.52 |
| Microcrystalline Cellulose | 19.23 | 96.55 |
| Mannitol | 1.01 | 5.07 |
| Ethylcellulose | 2.03 | 10.2 |
| Hypromellose, Type2910 | 0.43 | 2.16 |
| Sodium Starch Glycolate | 0.50 | 2.53 |
| Sodium Lauryl Sulfate | 0.50 | 2.53 |
| Povidone | 0.34 | 1.73 |
| Talc | 1.36 | 6.84 |
| Methacrylic acid copolymer, Type A (Eudragit® LI00) | 2.09 | 10.51 |
| Methacrylic acid Copolymer, Type B (Eudragit® SI00) | 4.25 | 21.33 |
| Triethyl Citrate | 1.82 | 9.16 |
| Croscarmellose Sodium | 0.69 | 3.46 |
| Magnesium Stearate | 0.05 | 0.25 |
| Purified water | N/A** | N/A** |
| Isopropyl alcohol | N/A** | N/A** |
| Acetone | N/A** | N/A** |
| Ethyl alcohol | N/A** | N/A** |
| Total | 100.00 | 502.13 |
| Hard Gelatin Capsules |  | 1 unit (size 00) |

*Carbidopa is supplied as a monohydrate; the quantity is equivalent to 47.50 mg carbidopa anhydrous accordingly.
**Evaporated during drying process.

Manufacture of Formulation

Four different component beads were manufactured for formulation IPX066-AH5(A). The qualitative and quantitative compositions for each component seed are summarized in Table 26.

TABLE 26

Qualitative and Quantitative Composition for 4 Component Beads in IPX066 Capsule Test Formulation

| Ingredients | Formulation Formulation Code IPX066-AH5(A) mg/capsule |
|---|---|
| Component I | |
| Carbidopa USP | 9.45* |
| Levodopa USP | 35.00 |
| Croscarmellose Sodium | 3.46 |
| Povidone | 1.23 |
| Magnesium Stearate | 0.25 |
| Purified Water, USP | N/A** |
| Component II | |
| Carbidopa USP | 7.43* |
| Levodopa USP | 27.50 |
| Microcrystalline Cellulose NF | 5.07 |
| Mannitol NF | 5.07 |
| Sodium Starch Glycolate NF | 2.53 |
| Sodium Lauryl Sulfate NF | 2.53 |
| Povidone USP | 0.50 |
| Methacrylic acid copolymer, Type A NF (Eudragit® L100) | 0.62 |
| Methacrylic acid Copolymer, Type B NF (Eudragit® S100) | 1.24 |
| Triethyl Citrate NF | 0.53 |
| Talc USP | 0.54 |
| Acetone, NF | N/A** |
| Isopropyl Alcohol, USP | N/A** |
| Purified Water, USP | N/A** |
| Component III | |
| Carbidopa USP | 34.41* |
| Levodopa USP | 127.50 |
| Microcrystalline Cellulose NF | 69.39 |
| Methacrylic acid copolymer, Type A NF (Eudragit® L100) | 2.79 |
| Methacrylic acid Copolymer, Type B NF (Eudragit® S100) | 5.72 |
| Triethyl Citrate NF | 2.45 |
| Talc USP | 2.44 |
| Acetone, NF | N/A** |
| Isopropyl Alcohol, USP | N/A** |
| Purified Water, USP | N/A** |
| Component IV | |
| Tartaric acid NF | 88.52 |
| Microcrystalline Cellulose NF | 22.09 |
| Ethylcellulose NF | 10.20 |
| Hypromellose Type 2910 USP | 2.16 |
| Methacrylic acid copolymer, Type A NF (Eudragit® L100) | 7.10 |
| Methacrylic acid Copolymer, Type B NF (Eudragit® S100) | 14.37 |
| Triethyl Citrate NF | 6.18 |
| Talc USP | 3.86 |
| Acetone, NF | N/A** |
| Isopropyl Alcohol, USP | N/A** |
| Purified Water, USP | N/A** |
| Hard Gelatin Capsule | 1 unit |
| Total Capsule Fill weight | 502.13 |

*Carbidopa is supplied as a monohydrate; the quantity is equivalent to 8.75, 6.88, 31.87 mg carbidopa anhydrous in component I, II, III, respectively.
**evaporated in drying process Manufacture of Component Bead I—CD/LD Ultra Fast Release Granules The required amounts of carbidopa, levodopa, croscarmellose sodium, and povidone were charged into a high shear granulator and mix until uniform. The mixed powder was granulated by adding the purified water. The granules were discharged and dried in the oven at 60±10° C. The LOD was measured using a Moisture Analyzer and the drying process was stopped when the LOD value is not more than a target value. The granules were crushed by using mortar and pestle. The crushed granules were passed through a US #18 mesh screen, and collect the granules that pass through 18 mesh screen. The collected granules were blended with magnesium stearate.

Manufacture of Component II—CD-LD Fast Release Beads Coated with Eudragit® S100:L100 (2:1)

Method of manufacture and process flow diagram of this component beads is the same as those of component 2 beads of formulation A in IPX066-AH4 except that mannitol is replaced by lactose.

Manufacture of Component III—CD-LD Slow Release Beads Coated with Eudragit® S100:L100 (2:1)

Method of manufacture and process flow diagram for this component beads is the same as those of the component 3 beads of formulation A in IPX066-AH4.

Manufacture of Component IV—TA Slow Release Beads Coated with Eudragit® S100:L100 (2:1)

Method of manufacture and process flow diagram for this component beads is the same as those of the component 5 beads of formulation A in IPX066-AH4.

Manufacture of the IPX066 Capsules for IPX066-AH5 (A)

The required amounts of the component beads were filled into hard gelatin capsules according to the specified target fill weights ±10%.

TABLE 27

Target Fill Weights of IPX066 Capsule Test Formulation

| Components | IPX066-AH5(A) mg/capsule |
|---|---|
| Component I Beads | 49.39 |
| Component II Beads | 53.56 |
| Component III Beads | 244.70 |
| Component IV Beads | 154.48 |
| Total Capsule Fill weight | 502.13 |

Example 9

The example describes the formulations IPX066-AH6 (A), and IPX066-AH6(B) and methods for making them.

TABLE 28

| | | Formulation | |
|---|---|---|---|
| | | IPX066-AH6(A) | IPX066-AH6(B) |
| | | Dosage strength | |
| Ingredients | % | 245 mg mg/capsule | 195 mg mg/capsule |
| Carbidopa | 10.21 | 66.14* | 52.64* |
| Levodopa | 37.84 | 245.00 | 195.00 |
| Tartaric acid | 17.63 | 132.53 | 105.48 |
| Microcrystalline Cellulose | 19.23 | 124.63 | 99.20 |
| Mannitol | 1.01 | 6.43 | 5.12 |
| Ethylcellulose | 2.03 | 15.27 | 12.15 |
| Hypromellose, Type2910 | 0.43 | 3.23 | 2.57 |
| Sodium Starch Glycolate | 0.50 | 3.21 | 2.55 |
| Sodium Lauryl Sulfate | 0.50 | 3.21 | 2.55 |
| Povidone | 0.34 | 2.52 | 2.01 |
| Talc | 1.36 | 9.45 | 7.52 |
| Methacrylic acid copolymer, Type A (Eudragit® L100) | 2.09 | 14.84 | 11.81 |
| Methacrylic acid Copolymer, Type B (Eudragit® S100) | 4.25 | 30.11 | 23.97 |
| Triethyl Citrate | 1.82 | 12.93 | 10.29 |

TABLE 28-continued

| | | Formulation | |
| --- | --- | --- | --- |
| | | IPX066-AH6(A) | IPX066-AH6(B) |
| | | Dosage strength | |
| Ingredients | % | 245 mg mg/capsule | 195 mg mg/capsule |
| Croscarmellose Sodium | 0.69 | 5.31 | 4.23 |
| Magnesium Stearate | 0.05 | 0.38 | 0.30 |
| Purified water | N/A** | N/A** | N/A** |
| Isopropyl alcohol | N/A** | N/A** | N/A** |
| Acetone | N/A** | N/A** | N/A** |
| Ethyl alcohol | N/A** | N/A** | N/A** |
| Total | 100.00 | 675.19 | 537.39 |
| Hard Gelatin Capsules | | 1 unit (size 00) | 1 unit (size 0EL) |

*Carbidopa is supplied as a monohydrate; the quantity is equivalent to 61.25 mg, 48.75 mg carbidopa anhydrous accordingly.
**evaporated during drying process.

Manufacture of Test Formulation

Four different component beads were manufactured for test formulation IPX066-AH6(A) and AH6(B). The qualitative and quantitative compositions for each component seed are summarized in Table 29.

TABLE 29

Qualitative and Quantitative Composition for 4 Component Beads in IPX066 Capsule Formulation

| Ingredients | IPX066-AH6(A) mg/capsule | IPX066-AH6(B) mg/capsule |
| --- | --- | --- |
| Component I | | |
| Carbidopa USP | 14.50* | 11.54* |
| Levodopa USP | 53.71 | 42.75 |
| Croscarmellose Sodium | 5.31 | 4.23 |
| Povidone | 1.89 | 1.50 |
| Magnesium Stearate | 0.38 | 0.30 |
| Purified Water, USP | N/A** | N/A** |
| Component II | | |
| Carbidopa USP | 9.42* | 7.50* |
| Levodopa USP | 34.87 | 27.75 |
| Microcrystalline Cellulose NF | 6.43 | 5.12 |
| Mannitol NF | 6.43 | 5.12 |
| Sodium Starch Glycolate NF | 3.21 | 2.55 |
| Sodium Lauryl Sulfate NF | 3.21 | 2.55 |
| Povidone USP | 0.63 | 0.51 |
| Methacrylic acid copolymer, Type A NF (Eudragit ® L100) | 0.79 | 0.63 |
| Methacrylic acid Copolymer, Type B NF (Eudragit ® S100) | 1.57 | 1.25 |
| Triethyl Citrate NF | 0.67 | 0.53 |
| Talc USP | 0.68 | 0.54 |
| Acetone, NF | N/A** | N/A** |
| Isopropyl Alcohol, USP | N/A** | N/A** |
| Purified Water, USP | N/A** | N/A** |
| Component III | | |
| Carbidopa USP | 42.22* | 33.60* |
| Levodopa USP | 156.42 | 124.50 |
| Microcrystalline Cellulose NF | 85.13 | 67.76 |
| Methacrylic acid copolymer, Type A NF (Eudragit ® L100) | 3.42 | 2.72 |
| Methacrylic acid Copolymer, Type B NF (Eudragit ® S100) | 7.02 | 5.59 |
| Triethyl Citrate NF | 3.01 | 2.39 |
| Talc USP | 2.99 | 2.38 |
| Acetone, NF | N/A** | N/A** |
| Isopropyl Alcohol, USP | N/A** | N/A** |
| Purified Water, USP | N/A** | N/A** |
| Component IV | | |
| Tartaric acid NF | 132.53 | 105.48 |
| Microcrystalline Cellulose NF | 33.07 | 26.32 |
| Ethylcellulose NF | 15.27 | 12.15 |
| Hypromellose Type 2910 USP | 3.23 | 2.57 |
| Methacrylic acid copolymer, Type A NF (Eudragit ® L100) | 10.63 | 8.46 |
| Methacrylic acid Copolymer, Type B NF (Eudragit ® S100) | 21.52 | 17.13 |
| Triethyl Citrate NF | 9.25 | 7.37 |
| Talc USP | 5.78 | 4.60 |
| Acetone, NF | N/A** | N/A** |
| Isopropyl Alcohol, USP | N/A** | N/A** |
| Purified Water, USP | N/A** | N/A** |
| Hard Gelatin Capsule | 1 unit | 1 unit |
| Total Capsule Fill weight | 675.19 | 537.39 |

*Carbidopa is supplied as a monohydrate
**evaporated in drying process.

Manufacture of Component Bead I—CD/LD Ultra Fast Release Granules

Method of manufacture and process flow diagram of this component beads is the same as those of component 1 beads of formulation A in IPX066-AH5 except that granules were dried by GPCG-1 instead of in an oven, and the granules were milled by Fitzmill instead of crushed by motor and pestle.

Manufacture of Component II—CD-LD Fast Release Beads Coated with Eudragit® S100:L100 (2:1)

Method of manufacture and process flow diagram of this component beads is the same as those of component 2 beads of formulation A in IPX066-AH5.

Manufacture of Component III—CD-LD Slow Release Beads Coated with Eudragit®S100:L100 (2:1)

Method of manufacture and process flow diagram for this component beads is the same as those of the component 3 beads of formulation A in IPX066-AH5.

Manufacture of Component IV—TA Slow Release Beads Coated with Eudragit® S100:L100 (2:1)

Method of manufacture and process flow diagram for this component beads is the same as those of the component 4 beads of formulation A in IPX066-AH5.

Manufacture of the IPX066 Capsules for IPX066-AH6(A) and (B)

The required amounts of the component beads were filled into hard gelatin capsules according to the specified target fill weights ±10%.

TABLE 30

Target Fill Weights of IPX066 Capsule Test Formulation.

| Components | IPX066-AH6(A) mg/capsule | IPX066-AH6(B) mg/capsule |
| --- | --- | --- |
| Component I Beads | 75.79 | 60.32 |
| Component II Beads | 67.91 | 54.05 |
| Component III Beads | 300.21 | 238.94 |
| Component IV Beads | 231.28 | 184.08 |
| Total Capsule Fill weight | 675.19 | 537.39 |

What is claimed is:

1. A method for treating Parkinson's disease comprising orally administering to a human patient in need of such treatment a multiparticulate formulation comprising about 10 mg to about 300 mg of carbidopa and about 25 mg to about 1200 mg of levodopa wherein the multiparticulate formulation comprises:
   a. an immediate release component comprising a mixture of carbidopa and levodopa in a ratio of about 1 to about 4; and
   b. a controlled release component comprising more than one bead, pellet or granule and at least one controlled release excipient that provides for the controlled release of carbidopa, levodopa and a carboxylic acid that is not carbidopa or levodopa from the bead, pellet or granule, wherein the molar ratio of carboxylic acid to levodopa is greater than 1:4 and less than 4:1, and following oral administration of the multiparticulate formulation the carbidopa, levodopa and carboxylic acid are released over a period of time of about 6 hours, and
   wherein following a single dose administration of the multiparticulate formulation the patient's levodopa plasma concentration profile comprises:
   (i) a time of administration;
   (ii) a first concentration that occurs at a first time and within one hour of the time of administration;
   (iii) a second concentration that occurs at a second time after said first time; and
   (iv) a third concentration that occurs after said second concentration and at a third time that is at least four hours after said second concentration, and the second concentration is the maximum concentration of levodopa in the profile; the first concentration is greater than or equal to about fifty percent of the second concentration; the peak-to-trough ratio of the second concentration to the third concentration is about 1.5 to about 2.5 and the levodopa plasma concentration decreases after the third concentration,
   wherein following a single dose administration of the multiparticulate formulation the levodopa blood plasma levels do not fluctuate more than 40% between 0.5 hours and six hours after administration, and
   wherein the administration of the multiparticulate formulation is effective in alleviating at least one symptom of Parkinson's disease.

2. The method of claim 1 wherein the disease is secondary Parkinsonism.

3. The method of claim 1 wherein the first concentration is about fifty percent of the second concentration.

4. The method of claim 1 wherein the third concentration occurs about four hours after the second concentration.

5. The method of claim 1 wherein the third concentration occurs about six hours after the time of administration.

6. The method of claim 1 wherein the second concentration occurs about one hour after the first concentration.

7. The method of claim 1 wherein the first, second and third concentrations are mean plasma concentrations.

8. The method of claim 1 wherein the first, second and third concentrations are median plasma concentrations.

9. The method of claim 1 wherein the multiparticulate formulation is administered three times a day.

10. The method of claim 9 wherein the multiparticulate formulation is administered every six hours.

11. The method of claim 1 wherein the carboxylic acid is selected from the group consisting of tartaric acid, adipic acid, succinic acid, citric acid, benzoic acid, acetic acid, ascorbic acid, edetic acid, fumaric acid, lactic acid, malic acid, oleic acid, sorbic acid, stearic acid, palmitic acid, boric acid and mixtures thereof.

12. The method of claim 11 wherein the carboxylic acid is tartaric acid.

13. The method of claim 1 wherein the carbidopa, levodopa and the carboxylic acid are in the same controlled release bead, pellet or granule.

14. The method of claim 1 wherein the carbidopa and levodopa are in different controlled release bead, pellet or granule from the carboxylic acid.

15. The method of claim 1 wherein the carboxylic acid and levodopa are present in the formulation in a carboxylic acid to levodopa molar ratio of greater than 1:4 and less than 3:2.

16. The method of claim 1 wherein the carboxylic acid and levodopa are present in the formulation in a carboxylic acid to levodopa molar ratio of greater than 1:2 and less than 4:3.

17. The method of claim 1 wherein the immediate release component and controlled release component are in a capsule.

18. The method of claim 1 wherein the controlled release component comprises at least two different populations of controlled release beads, pellets or granules wherein the first population of controlled release beads, pellets or granules exhibits a slower in vitro dissolution profile of levodopa compared to the second population of controlled release beads, pellets or granules.

19. The method of claim 1 wherein the molar ratio of carboxylic acid to levodopa is greater than 2:3 and less than 5:4.

20. A method for treating Parkinson's disease comprising orally administering to a human patient in need of such treatment a multiparticulate formulation comprising about 10 mg to about 300 mg of carbidopa and about 25 mg to about 1200 mg of levodopa wherein the multiparticulate formulation comprises:
   a. an immediate release component comprising a mixture of carbidopa and levodopa in a ratio of about 1 to about 4; and
   b. a controlled release component comprising at least two different populations of controlled release beads, pellets or granules comprising carbidopa and levodopa and a controlled release excipient, wherein a first population of controlled release beads, pellets or granules exhibits a slower in vitro dissolution profile of levodopa compared to a second population of controlled release beads, pellets or granules, and following oral administration of the multiparticulate formulation the carbidopa and levodopa are released from the controlled release component over a period of time of about 6 hours,
   wherein following a single dose administration of the multiparticulate formulation the patient's levodopa plasma concentration profile comprises:
   (i) a time of administration;
   (ii) a first concentration that occurs at a first time and within one hour of the time of administration;
   (iii) a second concentration that occurs at a second time after said first time; and
   (iv) a third concentration that occurs after said second concentration and at a third time that is about six hours after the time of administration, and the second concentration is the maximum concentration of levodopa in the profile; the first concentration is greater than or equal to about fifty percent of the second concentration;

the peak-to-trough ratio of the second concentration to the third concentration is about 1.5 to about 2.5 and the levodopa plasma concentration decreases after the third concentration, wherein following a single dose administration of the multiparticulate formulation the levodopa blood plasma levels do not fluctuate more than 40% between 0.5 hours and six hours after administration, and wherein the administration of the multiparticulate formulation is effective in alleviating at least one symptom of Parkinson's disease.

21. The method of claim 20 wherein the first population of controlled release beads, pellets or granules releases less than 20% of the levodopa after 120 minutes, less than 40% of levodopa after 150 minutes, less than 80% after 210 minutes, and 100% after 260 minutes of testing using a USP basket dissolution apparatus at 75 rpms with simulated gastric fluid medium for the first 120 minutes and simulated intestinal fluid thereafter.

22. The method of claim 20 wherein the second population of controlled release beads, pellets or granules comprise a core comprising carbidopa and levodopa and an enteric coating applied to the core.

23. A method for treating Parkinson's disease comprising orally administering to a human patient in need of such treatment a multiparticulate formulation comprising about 10 mg to about 300 mg of carbidopa and about 25 mg to about 1200 mg of levodopa wherein the multiparticulate formulation comprises:
  a. an immediate release component comprising a mixture of carbidopa and levodopa in a ratio of about 1 to about 4; and
  b. a controlled release component comprising more than one bead, pellet or granule and at least one controlled release excipient that provides for the controlled release of carbidopa, levodopa and tartaric acid from the bead, pellet or granule wherein the molar ratio of tartaric acid to levodopa is greater than 1:4 and less than 4:1 and wherein following a single dose administration of the multiparticulate formulation the patient's levodopa plasma concentration profile comprises:
  (i) a time of administration;
  (ii) a first concentration that occurs at a first time and within one hour of the time of administration;
  (iii) a second concentration that occurs at a second time after said first time; and
  (iv) a third concentration that occurs after said second concentration and at a third time that is at least four hours after said second concentration, and the second concentration is the maximum concentration of levodopa in the profile; the first concentration is greater than or equal to about fifty percent of the second concentration; the peak-to-trough ratio of the second concentration to the third concentration is about 1.5 to about 2.5 and the levodopa plasma concentration decreases after the third concentration, wherein following a single dose administration of the multiparticulate formulation the levodopa blood plasma levels do not fluctuate more than 40% between 0.5 hours and six hours after administration, and wherein the administration of the multiparticulate formulation is effective in alleviating at least one symptom of Parkinson's disease.

24. The method of claim 1 wherein the controlled release excipient comprises a coating that comprises an enteric polymer.

25. The method of claim 20 wherein the controlled release excipient comprises a coating that comprises an enteric polymer.

26. The method of claim 23 wherein the controlled release excipient comprises a coating that comprises an enteric polymer.

27. The method of claim 20 wherein the immediate release component and the controlled release component are in a capsule.

28. The method of claim 23 wherein the immediate release component and the controlled release component are in a capsule.

29. The method of claim 1 wherein the immediate release component and the controlled release component are sprinkled onto food or liquids for administration.

30. The method of claim 20 wherein the immediate release component and the controlled release component are sprinkled onto food or liquids for administration.

31. The method of claim 23 wherein the immediate release component and the controlled release component are sprinkled onto food or liquids for administration.

* * * * *